US012779241B2

(12) United States Patent
Faircloth

(10) Patent No.: US 12,779,241 B2
(45) Date of Patent: Nov. 3, 2026

(54) PHOTONIC TREATMENT AND DIAGNOSTIC SYSTEMS AND METHODS

(71) Applicant: Brian Faircloth, Evergreen, CO (US)

(72) Inventor: Brian Faircloth, Evergreen, CO (US)

( * ) Notice: Subject to any disclaimer, the term of this patent is extended or adjusted under 35 U.S.C. 154(b) by 788 days.

(21) Appl. No.: 17/473,352

(22) Filed: Sep. 13, 2021

(65) Prior Publication Data

US 2022/0080219 A1 Mar. 17, 2022

Related U.S. Application Data

(60) Provisional application No. 63/077,027, filed on Sep. 11, 2020.

(51) Int. Cl.
*A61N 5/06* (2006.01)

(52) U.S. Cl.
CPC .... *A61N 5/0601* (2013.01); *A61N 2005/0612* (2013.01); *A61N 2005/063* (2013.01)

(58) Field of Classification Search
CPC .......... A61N 5/0601; A61N 2005/0612; A61N 2005/063
See application file for complete search history.

(56) References Cited

U.S. PATENT DOCUMENTS

| | | | |
|---|---|---|---|
| 4,576,177 A | 3/1986 | Webster, Jr. | |
| 4,693,244 A | 9/1987 | Daikuzono | |
| 4,735,201 A | 4/1988 | O'Reilly | |
| 4,736,743 A | 4/1988 | Daikuzono | |
| 5,042,980 A | 8/1991 | Baker et al. | |
| 5,164,945 A | 11/1992 | Long et al. | |
| 5,275,596 A | 1/1994 | Long et al. | |
| 5,320,620 A | 6/1994 | Long et al. | |
| 5,342,355 A | 8/1994 | Long | |
| 5,445,608 A | 8/1995 | Chen et al. | |
| 5,476,461 A | 12/1995 | Cho et al. | |
| 5,549,600 A | 8/1996 | Chio | |
| 6,138,046 A * | 10/2000 | Dalton | A61N 5/0601 356/300 |
| 6,152,951 A | 11/2000 | Hashimoto et al. | |
| 8,357,146 B2 * | 1/2013 | Hennings | A61B 18/28 606/15 |
| 10,232,189 B2 | 3/2019 | Kuhn et al. | |
| 10,295,719 B2 | 5/2019 | Rose et al. | |
| 10,588,695 B2 | 3/2020 | Walsh et al. | |
| 10,675,482 B2 | 6/2020 | Agarwal et al. | |

(Continued)

FOREIGN PATENT DOCUMENTS

| | | |
|---|---|---|
| WO | 9210142 A1 | 6/1992 |
| WO | 9505214 A1 | 2/1995 |

OTHER PUBLICATIONS

International Search Report and Written Opinion for PCT App. No. PCT/US2021/050092 dated Feb. 7, 2022, 11 pages.

(Continued)

*Primary Examiner* — Rex R Holmes

(74) *Attorney, Agent, or Firm* — Acuity IP, LLC; Nathan S. Cassell

(57) ABSTRACT

Exemplary photonic treatment systems and methods involve placing a fiber optic, optionally coupled with an absorber mechanism or scatterer mechanism, within a tumor or other diseased tissue of a patient, and delivering photonic energy to the tumor or diseased tissue via the fiber optic.

11 Claims, 24 Drawing Sheets

(56) References Cited

U.S. PATENT DOCUMENTS

| | | | | |
|---|---|---|---|---|
| 2005/0165462 | A1* | 7/2005 | Bays | A61B 18/24 607/88 |
| 2006/0198418 | A1* | 9/2006 | Hama | G02B 6/262 372/6 |
| 2006/0253178 | A1 | 11/2006 | Masotti | |
| 2007/0260295 | A1 | 11/2007 | Chen et al. | |
| 2011/0249935 | A1* | 10/2011 | Hu | G02B 6/264 385/27 |
| 2012/0078160 | A1* | 3/2012 | McMillan | A61N 5/0603 604/20 |
| 2012/0209359 | A1 | 8/2012 | Chen et al. | |
| 2014/0316387 | A1* | 10/2014 | Harris | A61K 8/29 606/9 |
| 2016/0245990 | A1 | 8/2016 | Boyden et al. | |
| 2016/0374563 | A1 | 12/2016 | Hendriks et al. | |
| 2018/0239074 | A1* | 8/2018 | Rose | A61N 5/06 |
| 2019/0290360 | A1* | 9/2019 | Goodrich | A61N 5/062 |
| 2022/0016433 | A1 | 1/2022 | Faircloth | |

OTHER PUBLICATIONS

Invitation to Pay Additional Fees for PCT App. No. PCT/US2021/050092 dated Nov. 18, 2021, 2 pages.

* cited by examiner

PHOTONIC TREATMENT AND DIAGNOSTIC SYSTEMS AND METHODS

CROSS-REFERENCE

This application claims the benefit of U.S. Provisional Patent Application No. 63/077,027 filed Sep. 11, 2020, the content of which is incorporated herein by reference.

BACKGROUND

Embodiments of the present invention related generally to systems and methods for treating diseased tissue, and in particular, to treatment systems and methods for delivering photonic treatments to a patient presenting with a medical condition such as cancer, benign prostatic hyperplasia (BPH), endometriosis, and the like.

Various treatment devices and methods have been proposed for treating cancerous tumors and other diseased tissues. Often, such techniques require making incisions in the body of a patient, delivering ionizing radiation, or administering drugs.

Although these treatment modalities can provide relief to patients presenting with cancer tumors or other diseased tissues, still further improvements are desired. Embodiments of the present invention address at least some of these outstanding needs.

SUMMARY

Embodiments of the present invention encompass systems and methods for delivering photonic treatments to a cancerous tumor or other diseased tissue. Exemplary embodiments encompass the minimally invasive treatment of cancerous tumors or other diseased tissues that does not require an incision, harmful ionizing radiation, or drugs. Systems and methods disclosed herein enable the treatment of some cancers or other diseased tissues that are resistant to other treatments or considered difficult or impossible to treat otherwise. While primarily discussed herein with reference to the treatment of cancer, it is understood that the disclosed treatment modalities should not be limited to the treatment of cancer. For example, embodiments of the present invention encompass the treatment of any condition that can benefit from the application of intense heat or energy to a localized area inside the body, including benign prostatic hyperplasia (BPH), endometriosis, benign tumors, and the like.

Exemplary embodiments involve the treatment of diseased tissue (e.g. tumors) with no more invasiveness than one would encounter being stuck with a syringe needle. Exemplary embodiments do not require incisions or the use of catheters. In some cases, techniques disclosed herein can provide diagnostic feedback (e.g. spectral diagnostics) about or related to the treatment. In some cases, diagnostic information can relate to information obtained before the treatment during the treatment, and/or after the treatment.

In one aspect, embodiments of the present invention encompass systems and methods for treating a patient presenting with a cancerous tumor or other diseased tissue. Methods may include placing a fiber optic within the tumor or tissue of the patient and delivering photonic energy to the tumor or tissue via the fiber optic. In some cases, the fiber optic is coupled with an absorber mechanism. In some cases, an absorber mechanism can include a material such as graphite, steel, a steel alloy, copper, aluminum, silver, molybdenum, iron, titanium, gold, or various combinations thereof. In some cases, the fiber optic can be coupled with the absorber mechanism with an optical epoxy, a ceramic epoxy, soldering, brazing, or a cold weld. In some cases, the fiber optic can be coupled with a scatterer mechanism. In some cases, the scatterer mechanism includes a material such as ceramic alumina, zirconia, frosted glass, or various combinations thereof. In some cases, the fiber optic includes a core and one or more clads. In some cases, a needle is inserted into the patient, and the step of placing the fiber optic within the tumor of the patient includes advancing the fiber optic within the inserted needle.

In another aspect, a system or method for treating a patient presenting with a diseased tissue can include placing a fiber optic within the diseased tissue of the patient and delivering photonic energy to the diseased tissue via the fiber optic. In some cases, the fiber optic includes a core having a first refractive index and a clad having a second refractive index that is less than the first refractive index. In some cases, an evanescent electromagnetic field extends past a total internal reflection boundary of the clad and generates heat in absorptive tissue near the fiber optic. In some cases, the fiber optic includes a core, a clad disposed peripherally to the core, and an absorbing material disposed peripherally to the clad. In some cases, an evanescent electromagnetic field extends past a total internal reflection boundary of the clad and generates heat in the absorbing material. In some cases, the fiber optic includes a core, a first clad, and a second clad. In some cases, the first clad is disposed peripherally to the core, and the second clad is disposed peripherally to a covered portion of the first clad. In some cases, an evanescent electromagnetic field extending past a total internal reflection boundary of the first clad is contained in the second clad where the second clad is disposed peripherally to the covered portion of the first clad. In some cases, an evanescent electromagnetic field extending past a total internal reflection boundary of the first clad generates heat in absorptive tissue near the fiber optic at a location near an uncovered portion of the first clad that is adjacent to the covered portion of the first clad.

In another aspect, embodiments of the present invention encompass systems and methods for analyzing a tissue of a patient. Exemplary systems and methods can include placing a fiber optic near the tissue of the patient, and transmitting multispectral interrogation light through the fiber optic, such that the multispectral interrogation light exits a distal end of the fiber optic, travels toward the tissue, and is reflected by the tissue. Systems and methods may also involve receiving reflected light at the distal end of the fiber optic from the tissue, and analyzing the tissue based on the reflected light. In some cases, the step of transmitting the multispectral light through the fiber optic includes transmitting the multispectral light through a core of the fiber optic. In some cases, the step of receiving reflected light at the distal end of the fiber optic includes receiving at least a portion of the reflected light through a clad of the fiber optic. In some cases, the clad is a first clad that is disposed peripherally to the core, and the fiber optic further includes a second clad that is disposed peripherally to the first clad and that inhibits leakage of the reflected light. In some cases, the step of transmitting the multispectral light through the fiber optic includes transmitting the multispectral light through a first plurality of cores of the fiber optic. In some cases, the step of receiving the reflected light includes receiving the reflected light through a second plurality of cores of the fiber optical. In some cases, systems and methods can also involve delivering working photonic energy to the tissue. In some cases, the working photonic energy is delivered to the tissue via the fiber optic. In some cases, the fiber optic is a tandem fiber optic. In some cases, working photonic energy is delivered to the tissue via a power delivering fiber optic. In some cases, the multispectral techniques as described herein can be carried out instead with a single wavelength. For example, single wavelength embodiments can utilize Raman spectroscopy analysis.

In still another aspect, embodiments of the present invention encompass systems for treating a patient presenting with a diseased tissue. Exemplary systems include a light source, a fiber optic in operative association with the light source, and an absorber mechanism or a scatter mechanism coupled with the fiber optic. In some cases, the fiber optic is configured to delivery photonic energy from the light source to the absorber mechanism or the scatter mechanism to treat the diseased tissue of the patient.

In yet another aspect, embodiments of the present invention encompass systems for analyzing a tissue of a patient. Exemplary systems include a light source, a fiber optic in operative association with the light source, and a spectral analyzer mechanism. In some cases, the fiber optic is configured to transmit multispectral interrogation light from the light source to the tissue, such that reflected light returns from the tissue. In some cases, the spectral analyzer is configured to analyze the reflected light returning from the tissue.

BRIEF DESCRIPTION OF THE DRAWINGS

The novel features of the invention are set forth with particularity in the appended claims. A better understanding of the features and advantages of the provided system and methods will be obtained by reference to the following detailed description that sets forth illustrative embodiments, in which the principles of the invention are utilized, and the accompanying drawings of which:

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Embodiments of the present invention encompass photonic systems and methods for heating or treating tissue. For example, a powerful light source, such as a high intensity lamp, LED, or laser can be used to deliver power through a fiber optic to tissue. In some cases, the power can be delivered in a precise manner to a discrete location on or within the tissue. In some cases, power can be delivered locally to tissue (e.g. a tumor or other diseased tissue). In some cases, embodiments of the present invention encompass the delivery of a vaporization heat flux density locally inside the body without an invasive procedure.

Figure 1B:
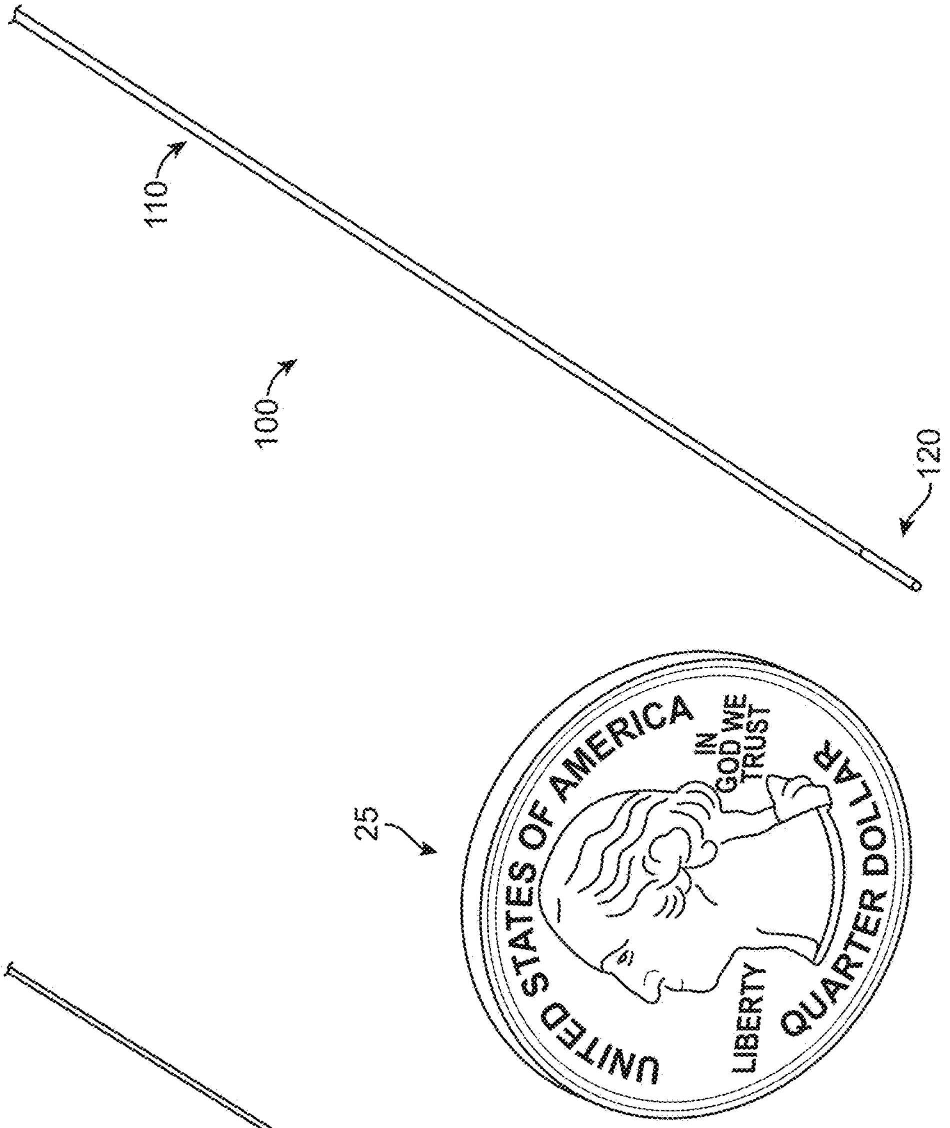
FIGS. 1A and 1B illustrate aspects of photonic treatment or fiber optic probe devices, according to embodiments of the present invention.
Figure 1A:
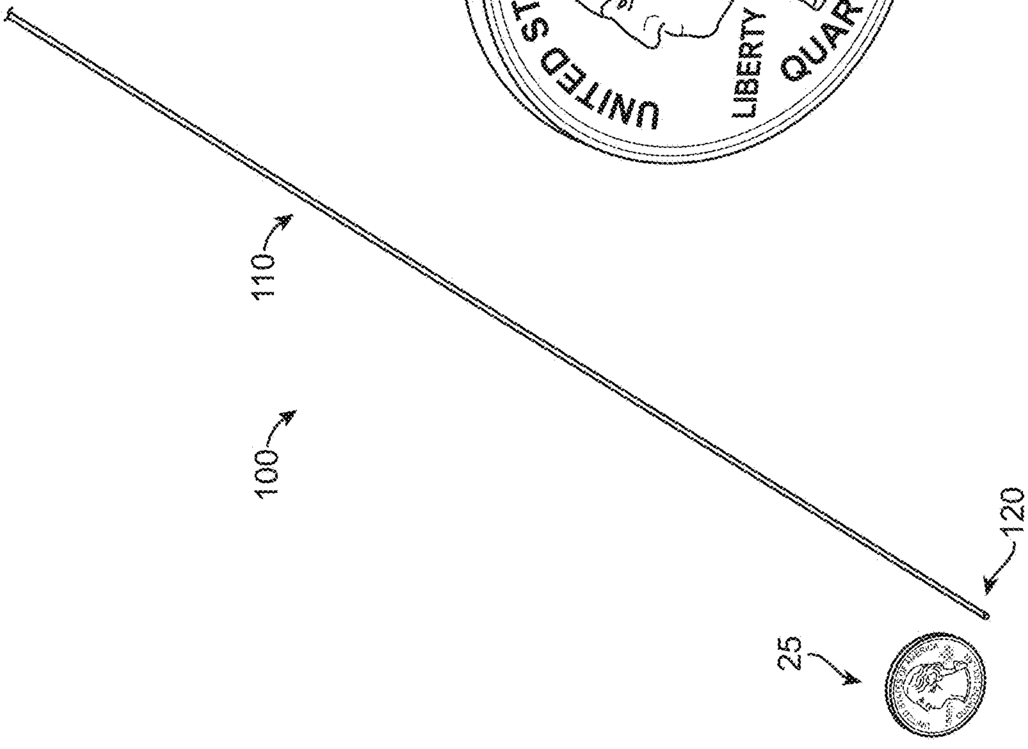

Turning now to the drawings, FIGS. 1A and 1B depict aspects of a photonic treatment or fiber optic probe device 100 that includes a fiber optic 110 in operative association with an absorber mechanism 120 or a scatterer mechanism 120. In some embodiments, the fiber optic 110 is a 400/440 μm index guided silica fiber. Other exemplary fiber optics for use in embodiments of the present invention can have core diameters from 8 μm all the way up to 1500 μm. Custom diameter fibers can be used as well. The enlarged view of FIG. 1B provides a conveniently viewable size comparison between device 100 and a U.S. quarter dollar coin 25. In some instances, mechanism 120 can operate as an absorber. In some instances, mechanism 120 can operate as a scatterer. In some embodiments the terms absorber (or absorbing) and scatterer (or scattering) can be used interchangeably. In some embodiments, the terms photonic treatment device and fiber optic probe device can be used interchangeably with the terms heat source, light source, heat device, and light device.

Figure 2A:
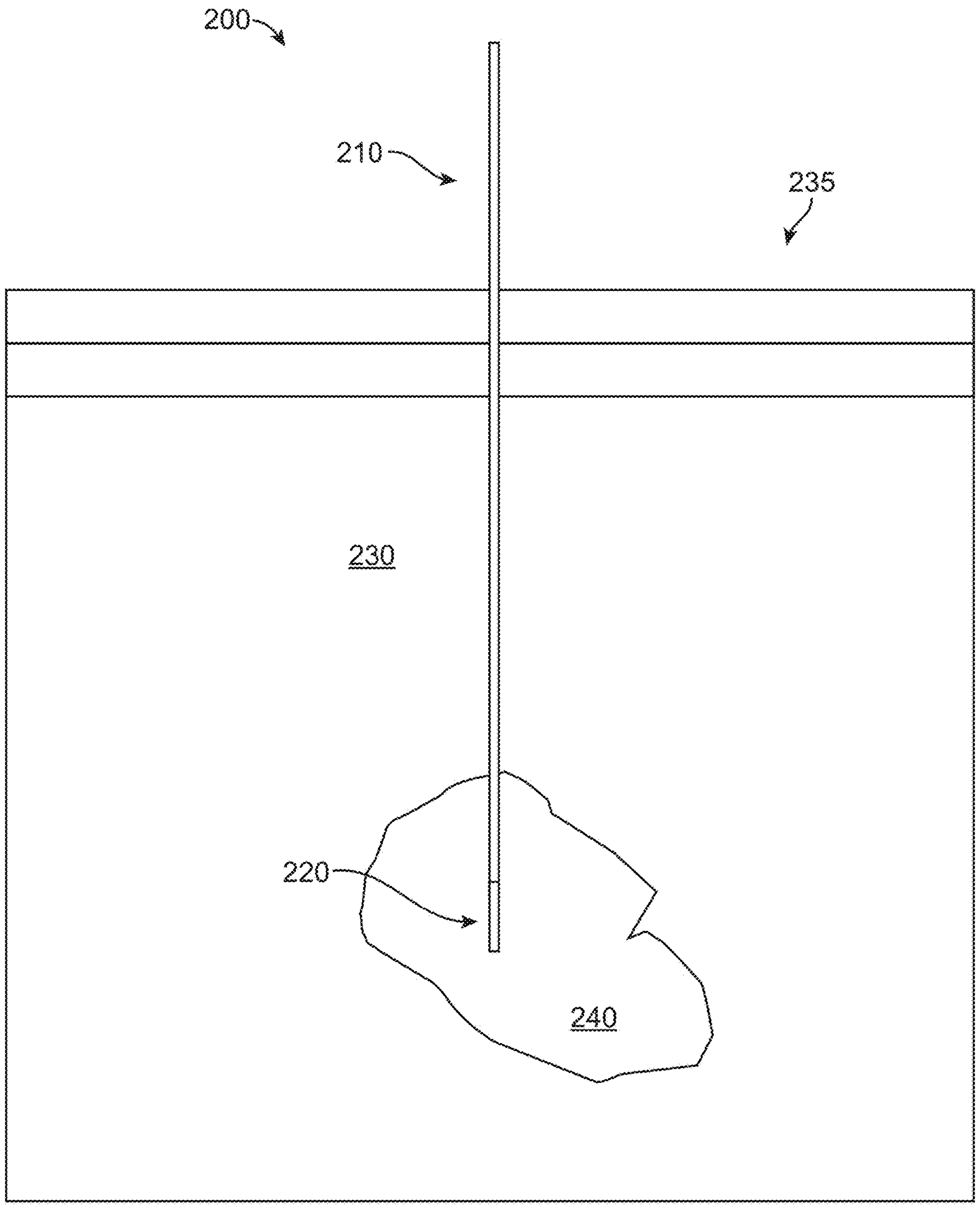
FIGS. 2A and 2B illustrate aspects of photonic treatment or fiber optic probe device techniques, according to embodiments of the present invention.

FIG. 2A illustrates aspects of basic placement of a heat/light source or device 200, according to embodiments of the present invention. As shown here, the heat/light source or device 200 can include a fiber optic 210 in operative association with an absorber/scatterer 220. Exemplary fiber optics can be made from glass or glass-like materials, and because of their small size and high aspect ratios they are remarkably strong. Fused silica can be used as a material for the fiber optic. In some cases, such fiber optics can have a bulk modulus of 41 GPa, a shear modulus of 31 GPa, a compressive Strength of 1108 MPa, and a hardness of 600 $kg/mm^2$. Exemplary fibers can be very flexible. Glass fibers may be bent into small diameters without breaking. Even modestly large fiber optics, for example fiber optics having 400 μm diameter cores, may be bent into coils less than one inch in diameter without breaking. The smaller the glass diameter of the fiber, the smaller the bend radius may be. Because of their strength, flexibility, and small size a fiber optic may be inserted directly into soft tissue in most cases as though it is its own insertion device. A 400/440 μm (core/clad) fiber is smaller in diameter than a 26 gauge syringe needle.

Fiber optics may also be made from polymers/plastics. In some cases, plastic fibers may not provide the same strength, heat resistance, or power handling capabilities as glass fibers, yet they may be desirable for use in certain embodiments. The small diameter and natural strength of the fiber optic can allow for the fiber optic to be inserted directly into the body, or the fiber optic could be collocated inside the inner diameter of a syringe needle or other conduit if more protection of the fiber is desired. In the case of vaporization, the syringe can be used to suction the ablated or vaporized tissue material in process. In many instances, fiber optics are non-magnetic. Exemplary treatment systems and methods can involve the use of fiber optics for inserting and/or removing magnetic hyperthermia treatment particles/structures, such as those described in U.S. patent application Ser. No. 17/379,433 filed Jul. 19, 2021, the content of which is incorporated herein by reference.

An absorber 220 such as graphite (or any number of other high absorption materials, including metals) can be attached to the end of the fiber 210 to absorb the incoming light and convert it to heat, thus heating the tissue locally. Metals exhibit absorption of light to varying degrees depending on the incident wavelength. A metal such as a steel alloy can be used for a large range of wavelengths. If short wavelengths are used (UV or blue for instance), metals such as copper or gold can be used as absorbers. Advantageously, gold exhibits chemical inertness and a lack of toxicity to the human body.

In some cases, a scatterer mechanism 220 can be provided as a single or monolithic element. A single element scatterer mechanism 220 can have an outer diameter that is approximately the same as (or nearly the same as) the diameter of the outer diameter of the fiber optic 210. In some cases, the single element scatterer can be provided with no further assemblies or devices around the fiber. Such configurations can facilitate a minimally invasive delivery of optical light to the treatment zone.

As shown in FIG. 2A, the device 200 can be delivered directly from the outside of the patient through the tissue 230 (e.g. through the skin 235) without requiring the use of a catheter. In some cases, the device 200 punctures the skin 235 when force is applied to the device, for example by an operator such as a surgeon or doctor, or by a surgical robotic system. As shown here, a method of treating a patient presenting with a diseased tissue, for example a cancerous tumor 240, can include placing a fiber optic 210 within the diseased tissue 240 of the patient, and delivering photonic energy to the diseased tissue via the fiber optic 210. In some instances, the fiber optic 210 is coupled with an absorber mechanism 220. In some instances, the fiber optic 210 is coupled with a scatterer mechanism 220. In the embodiment depicted here, the diseased tissue 240 can be considered as a target tissue for treatment.

Figure 2B:
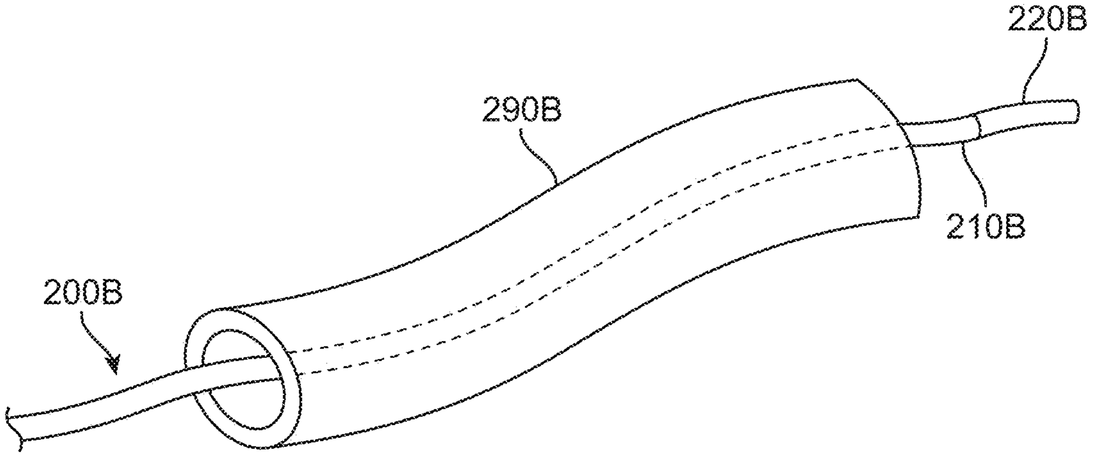

FIG. 2B illustrates aspects of basic placement of a heat/light source or device 200B, according to embodiments of the present invention. As shown here, the heat/light source or device 200B can include a fiber optic 210B in operative association with an absorber/scatterer 220B. The device 200B can be placed, advanced, and/or retracted within a catheter 290B. The fiber optic 210B can be as flexible as the catheter 290B. In such catheter embodiments, the device 200B can be maneuvered to various desired locations within the patient's body, such as the vasculature or other lumens, cavities, or passages. For example, the catheter 290B can be placed in the patient's body, and the device 200B can delivered or placed via the catheter to treat or otherwise deliver photonic energy to vascular tissue, cardiovascular tissue, urological tissue, gastrointestinal tissue, neurovascular tissue, ophthalmic tissue, or any other desired or target tissue of a patient.

Figure 3:
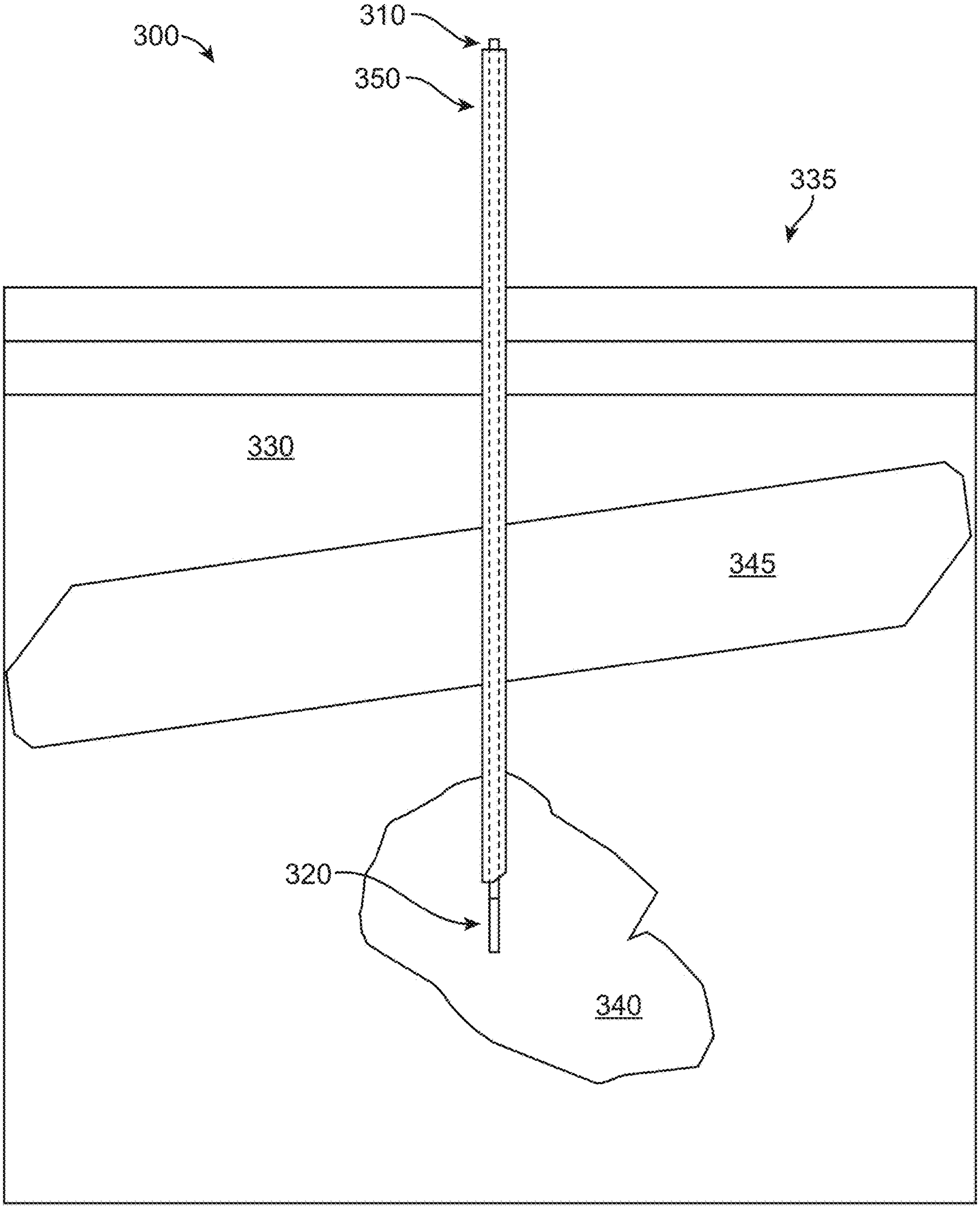
FIG. 3 illustrates aspects of photonic treatment or fiber optic probe devices, according to embodiments of the present invention.

FIG. 3 depicts aspects of basic placement for a heat/light source or device 300, according to embodiments of the present invention. The fiber optic 310 of the device 300 can fit inside of a syringe needle 350, and this combination is particularly well suited for treatments where harder tissue 345 (e.g. bone) must be penetrated to reach the area or target tissue 340 to be treated. A 400/440 μm fiber will fit inside of a 21.5-gauge or larger syringe needle. In some cases, the fiber 310 is stripped of any polymer coatings and only the core and clad are retained, before the fiber 310 is placed inside of the needle 350. In some cases, the fiber optic 310 has an outer diameter, and the needle 350 (or other insertion device) has an inner diameter that is approximately the same as (e.g. slightly larger than) the outer diameter of the fiber optic 310. In some cases the inner diameter of the needle is substantially or sufficiently larger than the outer diameter of the fiber to allow for suction and removal of the treated tissue via the syringe needle. This is especially useful in the case of tissue ablation and vaporization.

As shown in FIG. 3, the device 300 can be delivered directly from the outside of the patient through the tissue 330 (e.g. by puncturing the skin 335) without requiring the use of a catheter. As illustrated here, a method of treating a patient presenting with a diseased tissue 340, for example a cancerous tumor, can include placing a fiber optic 310 within the diseased tissue of the patient, and delivering photonic energy to the diseased tissue via the fiber optic. In some instances, the fiber optic is coupled with an absorber mechanism 320. In some instances, the fiber optic is coupled with a scatterer mechanism 320. In the embodiment depicted here, the diseased tissue 340 can be considered as a target tissue for treatment.

Figure 4B:
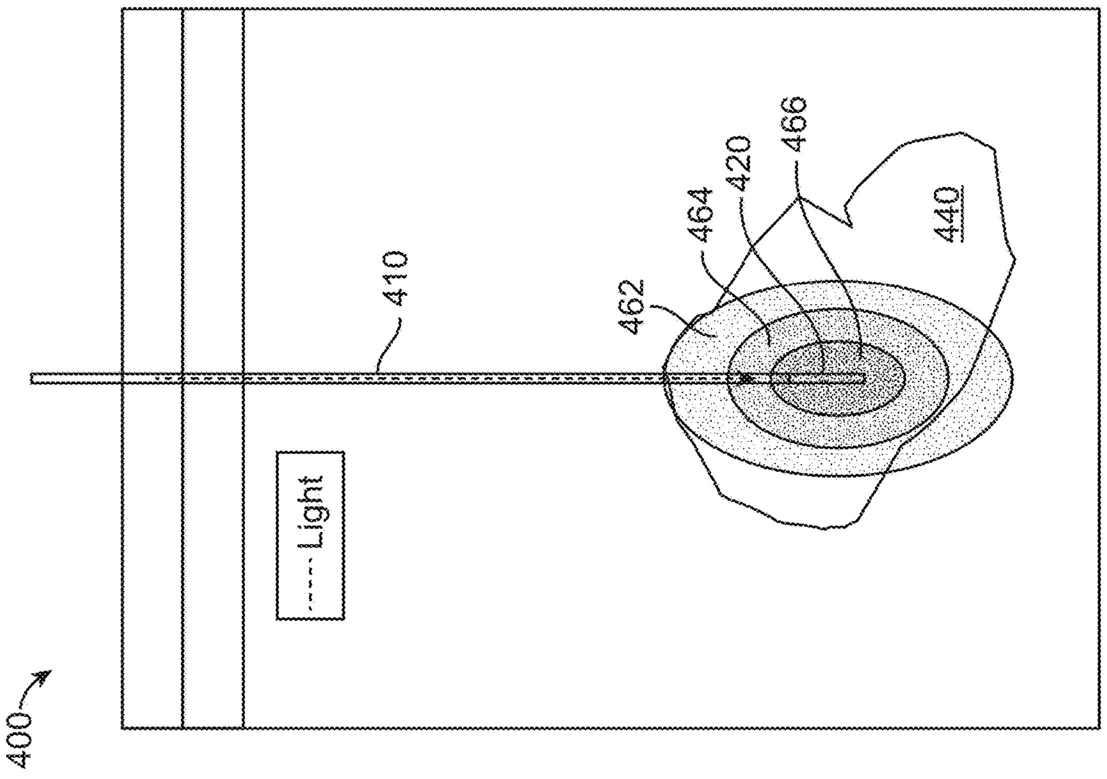
FIGS. 4A and 4B illustrate aspects of photonic treatment or fiber optic probe devices, according to embodiments of the present invention.
Figure 4A:
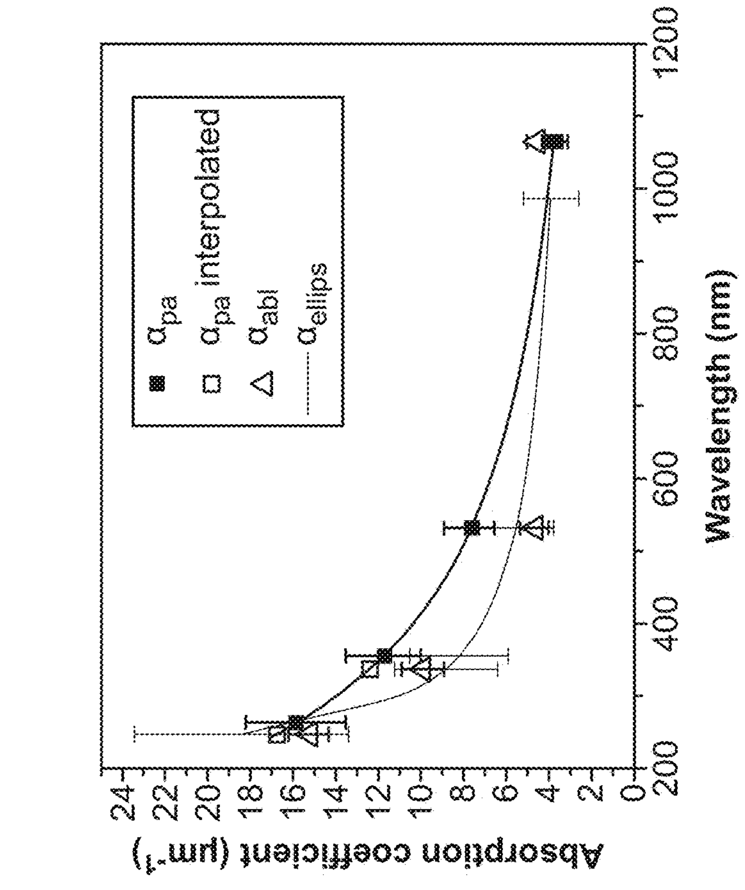

FIGS. 4A and 4B depict aspects of an absorber heating method. Specifically, FIG. 4A illustrates absorption coefficient features (e.g. absorption curve) of an exemplary absorber material such as graphite. FIG. 4B illustrates aspects of a device 400 that is used to provide heat energy to a target tissue 440, such as a tumor. Light, as depicted by a dashed line, can be passed down the fiber optic 410 and absorbed in an absorbing media 420 at the distal end of the fiber 410. The light energy can be converted into heat energy which heats the surrounding local tissue. In some instances, the heating provides, in relative degrees, a high temperature zone 462, a higher temperature zone 464, and a highest temperature zone 466. Hence, as shown in FIG. 4B, a method of treating a patient presenting with a diseased tissue 440, for example a cancerous tumor, can include placing a fiber optic 410 within the diseased tissue of the patient, and delivering photonic energy to the diseased tissue 440 via the fiber optic 410. In some instances, the fiber optic 410 is coupled with an absorber mechanism 420. In some instances, the fiber optic is coupled with a scatterer mechanism 420. In the embodiment depicted here, the diseased tissue 440 can be considered as a target tissue for treatment. Graphite can be used as an absorber material. Graphite absorbs most visible wavelengths of light as well as near infrared allowing for the use of a wide range of light sources. Additionally, graphite is a highly thermally conductive material (~470 W/K-m), thus able to spread the heat throughout the thermal body quickly.

Figure 5B:
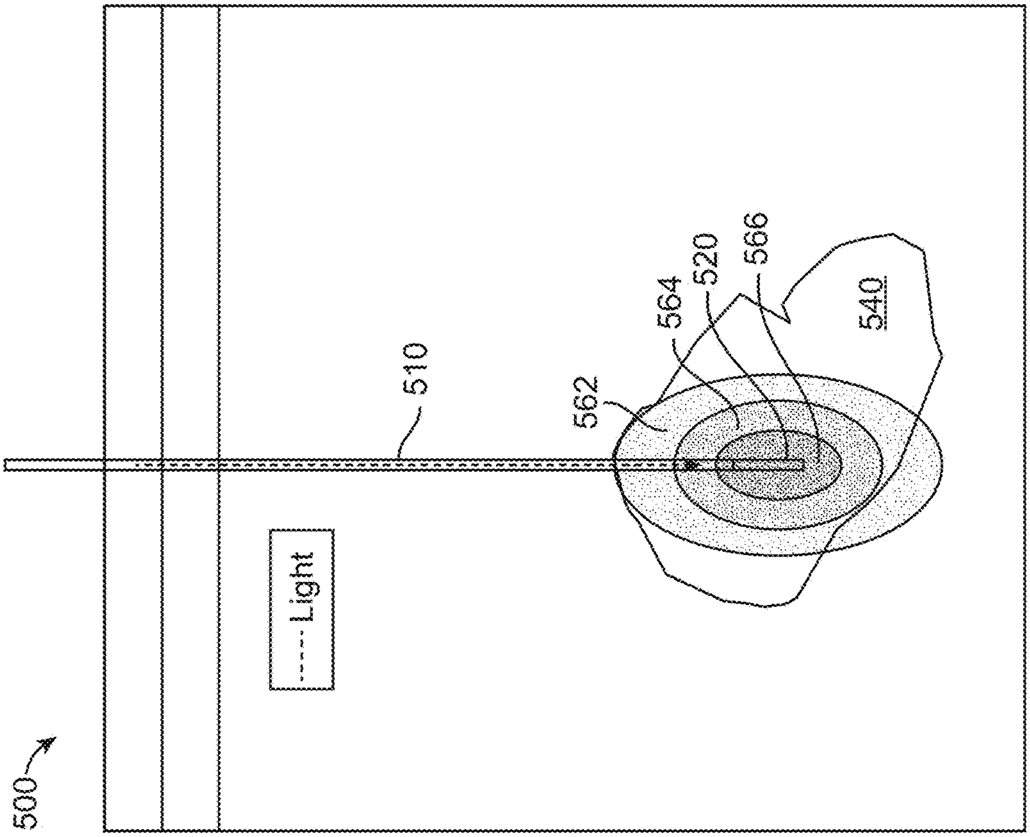
FIGS. 5A and 5B illustrate aspects of photonic treatment or fiber optic probe devices, according to embodiments of the present invention.
Figure 5A:
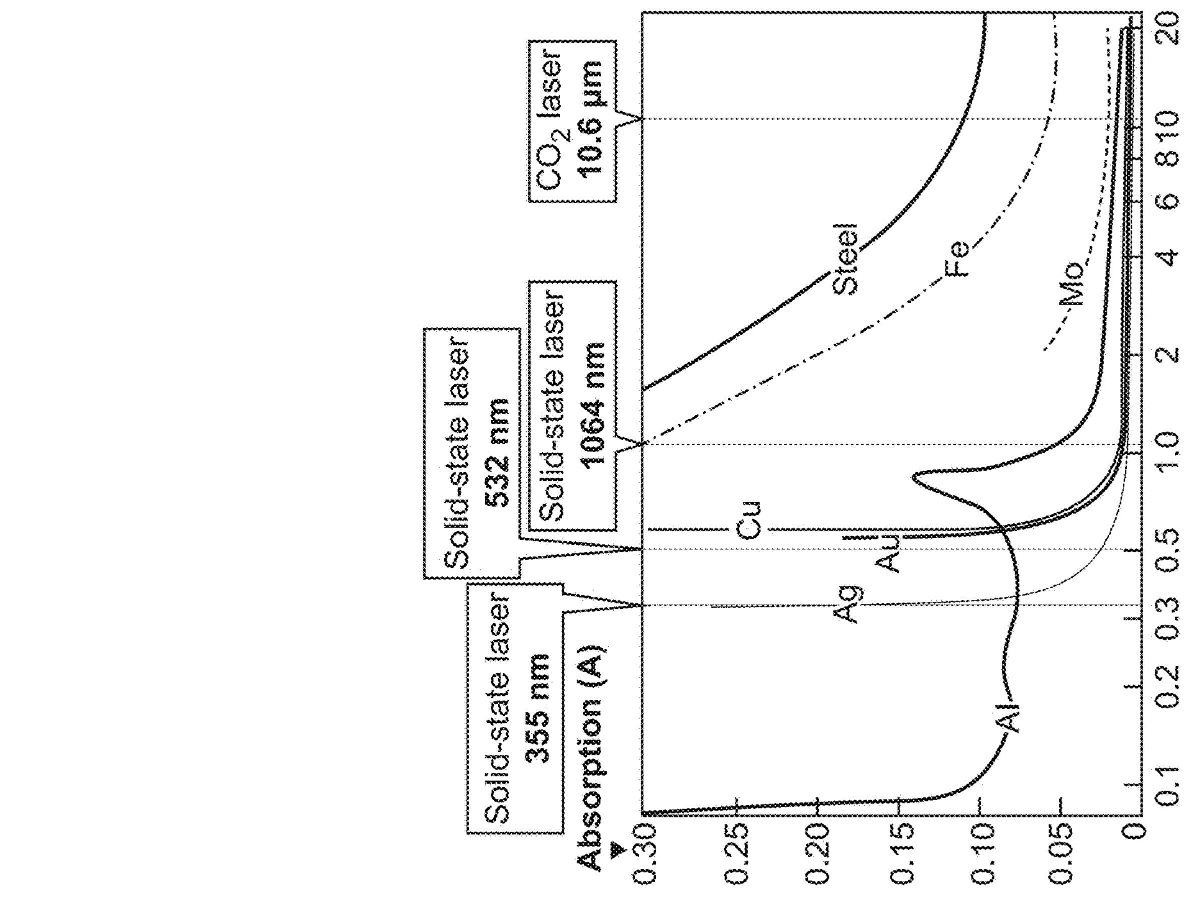
Figure 6A:
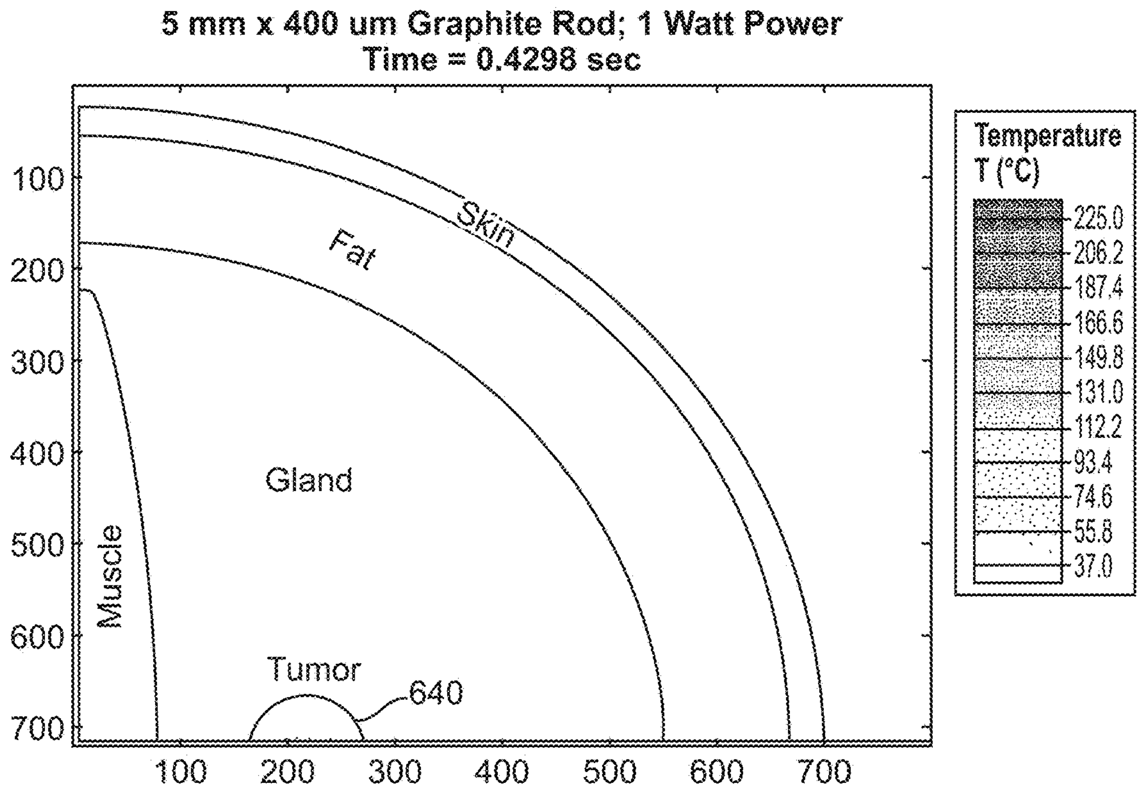
FIGS. 6A to 6D depict aspects of photonic treatment methods, according to embodiments of the present invention.
Figure 6B:
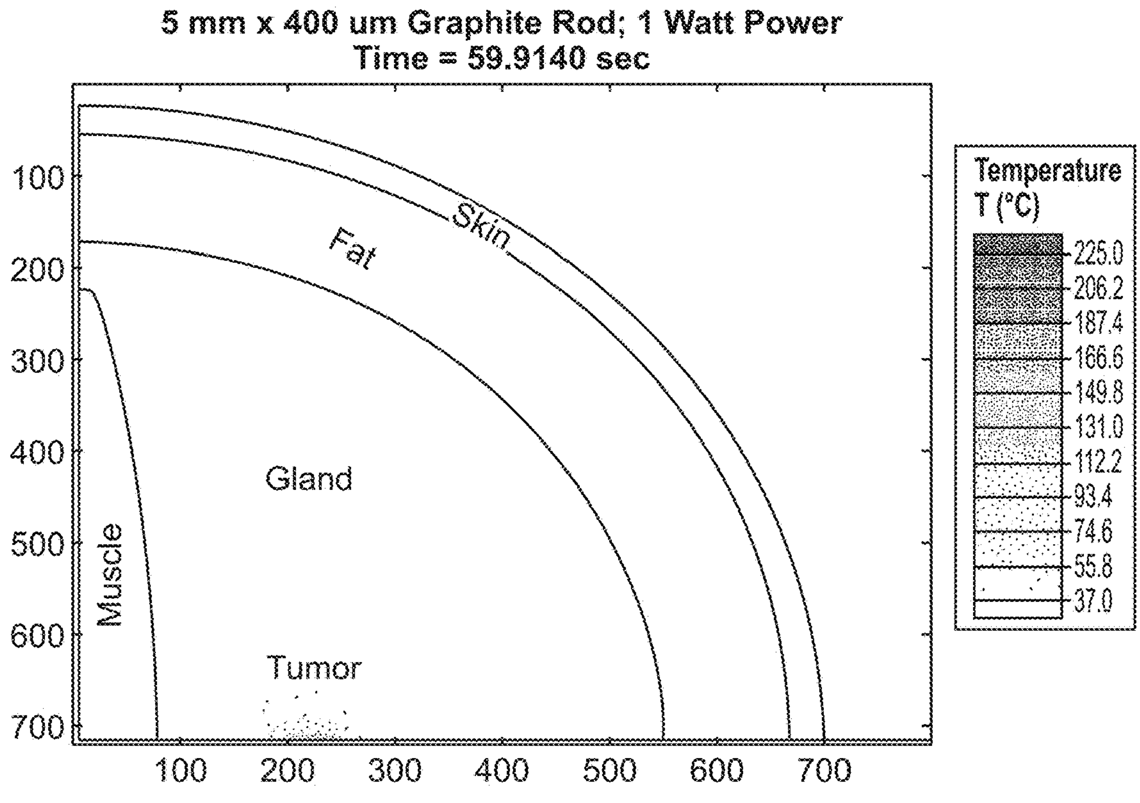
Figure 6C:
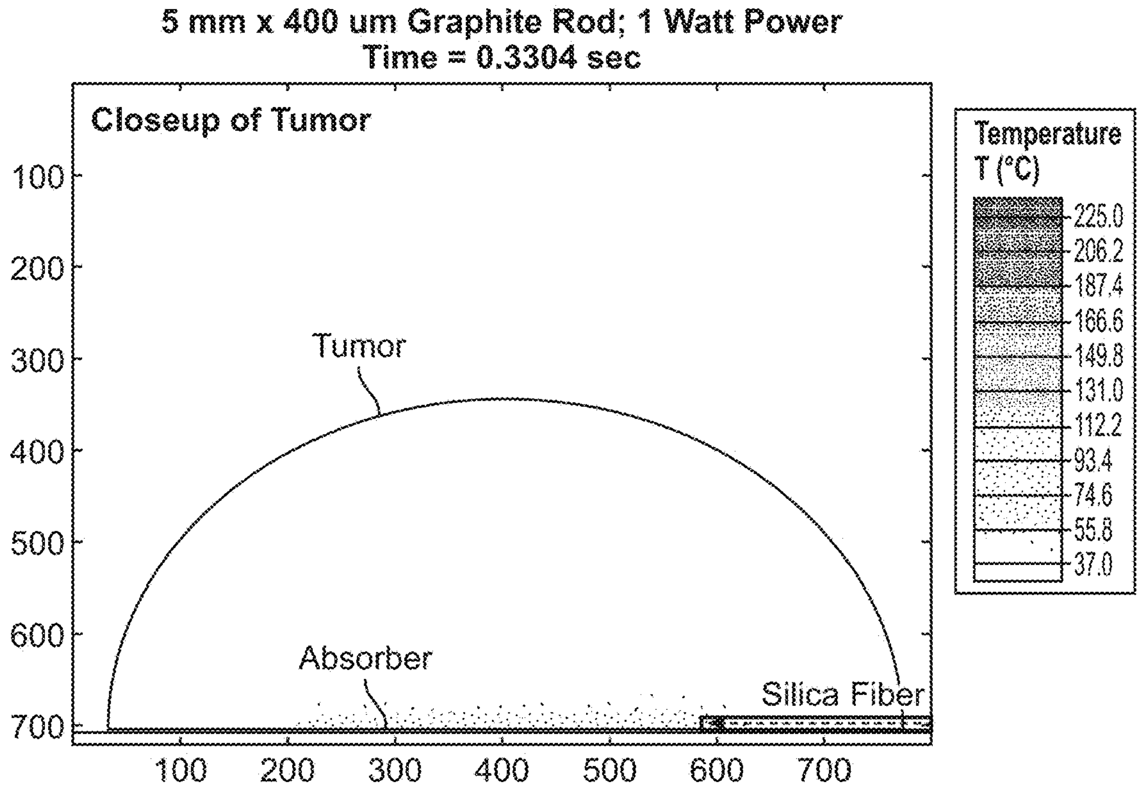
Figure 6D:
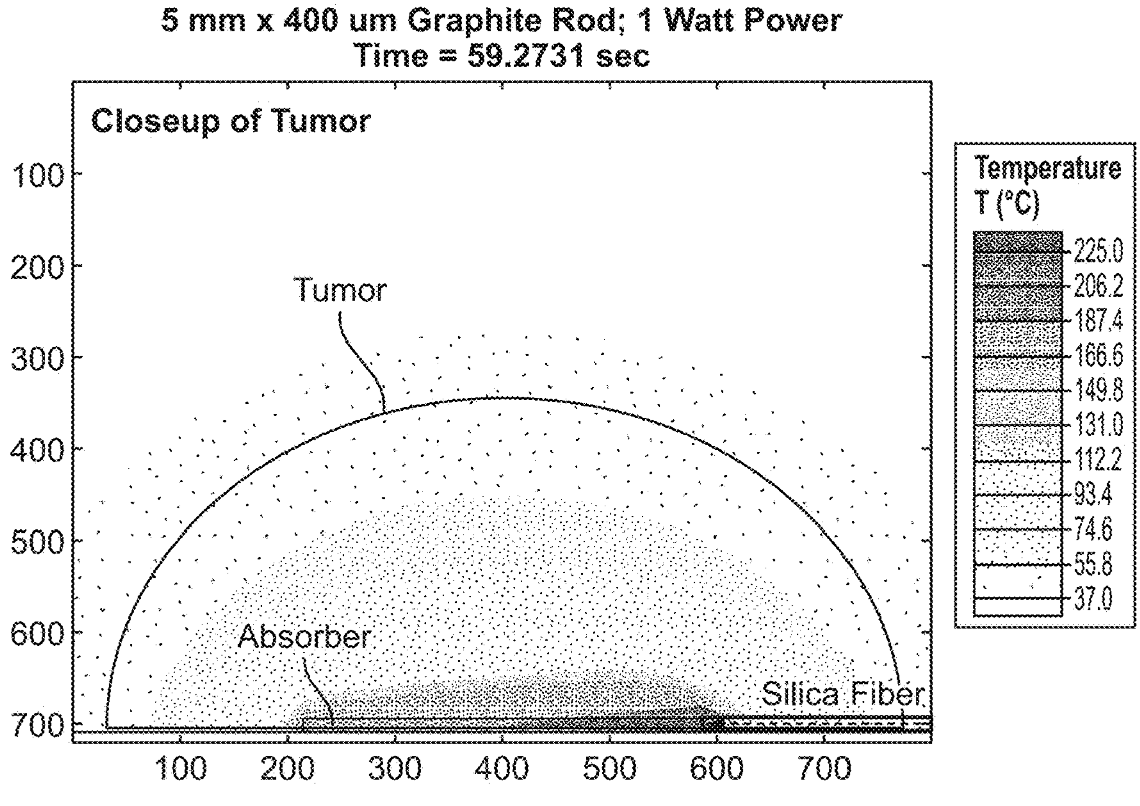

FIGS. 5A and 5B depicts aspects of an absorber heating method. Specifically, FIG. 5A illustrates absorption characteristics of exemplary absorber materials used in combination with various types of lasers. FIG. 5B illustrates aspects of a device 500 that is used to provide heat energy to a target tissue 540, such as a tumor. Metals (e.g. aluminum, silver, gold, copper, molybdenum, iron, and/or steel) can be used as an absorption material. Metals generally have high thermal conductivities and can spread the heat quickly throughout the absorber 420. Absorption in metals can be a function of the type of metal and the wavelength. According to some embodiments, the lower the wavelength the stronger the absorption. UV lamps or lasers in the visible/UV range can be used as a light source. In some cases, UV light can cause solarization in fibers which can limit the power. In some cases, solarization resistant fiber optics can be used. In some instances, the heating provides, in relative degrees, a high temperature zone 562, a higher temperature zone 564, and a highest temperature zone 566. Hence, as shown in FIG. 5B, a method of treating a patient presenting with a diseased tissue 540, for example a cancerous tumor, can include placing a fiber optic 510 within the diseased tissue of the patient, and delivering photonic energy to the diseased tissue 540 via the fiber optic 510. In some instances, the fiber optic 510 is coupled with an absorber mechanism 520. In some instances, the fiber optic 510 is coupled with a scatterer mechanism 520. In the embodiment depicted here, the diseased tissue 540 can be considered as a target tissue for treatment.

Gold is chemically inert, has a minimal impact on the human body, and can be used as an absorber material. In a device where gold is used, a frequency tripled YAG laser (355 nm) can be used. Blue diode lasers (~450 nm) may also be used, and may provide certain cost and/or size advantages. Titanium is also a good candidate material for use in or as an absorber mechanism.

Hence, in some methods, light can escape naturally from the fiber optic in a cone angle, called the numerical aperture (NA). In some methods, a diffuse scatterer (e.g. alumina or zirconia ceramic or frosted glass) can be attached at the end of the fiber and the light can scatter in an isotropic manner. In either case, this can allow the light to penetrate into the tissue and be absorbed naturally in the tissue at the natural absorption rate of the tissue. This can spread the heat load over a larger volume rather than being concentrated at the absorber, thus allowing for a more diffuse and potentially deeper heating profile. Additionally, photosensitive absorbers could be injected into the tissue beforehand to enhance or control the absorption levels. This technique may not involve attaching photosensitive material to the cells in question and decomposing the material through light exposure into a toxic compound as is done in photodynamic therapy (PDT). Exemplary embodiments can involve dyeing the tissue (e.g. with photosensitive absorbers or other dyes) to enhance differentiated absorption of the light from other tissue, and thus heat flux generated preferentially to the tissue in question. In some embodiments, a medical device pigment (e.g. such as any FDA approved medical device pigment enumerated in FDA 21 CFR 73 Subpart D) may be used to tailor the light absorption characteristics and differentiate the diseased tissue from surrounding tissue. In some cases, a photosensitive absorber or dye can include any one or more of the following: 1,4-Bis[(2-hydroxyethyl)amino]-9,10-anthracenedione bis(2-methyl-2-propenoic)ester copolymer, 1,4-Bis[(2-methylphenyl)amino]-9,10-anthracenedione, 1,4-Bis[4-(2-methacryloxyethyl) phenylamino] anthraquinone copolymer, Carbazole violet, Chlorophyllin-copper complex, oil soluble, Chromium-cobalt-aluminum oxide, Chromium oxide green, C.I. Vat Orange 1, 2-[[2,5-Diethoxy-4-[(4-methylphenyl)thiol]phenyl]azo]-1,3,5-benzenetriol, 16,23-Dihydrodinaphtho[2,3-a:2',3'-i] naphth [2',3':6,7] indolo [2,3-c] carbazole-5,10,15,17,22,24-hexone, N,N'-(9,10-Dihydro-9,10-dioxo-1,5-anthracenediyl) bisbenzimide, 7,16-Dichloro-6,15-dihydro-5,9,14,18-anthrazinetetrone, 16,17-Dimethoxydinaphtho [1,2,3-cd:3',2',1'-lm] perylene-5,10-dione, Poly(hydroxyethyl methacrylate)-dye copolymer, 4-[(2,4-dimethylphenyl)azo]-2,4-dihydro-5-methyl-2-phenyl-3H-pyrazol-3-one, 6-Ethoxy-2-(6-ethoxy-3-oxobenzo[b]thien-2(3H)-ylidene) benzo[b]thiophen-3 (2H)-one, Phthalocyanine green, Iron oxide, Titanium dioxide, Vinyl alcohol/methyl methacrylate-dye reaction product, Mica-based pearlescent pigment, and Disodium 1-amino-4-[[4-[(2-bromo-1-oxoallyl)amino]-2-sulfonatophenyl]amino]-9,10-dihydro-9,10-dioxoanthracene-2-sulfonate.

FIGS. 6A to 6D depict aspects of an absorber thermal simulations (breast model). The model is axisymmetric around the horizontal axis. The absorber (e.g. 5 mm×400 μm graphite rod) reaches 225° C. in 60 seconds with one watt of power absorption. The absorber can be placed in the tumor. As shown here, the absorber is coupled with or in operative association with a fiber optic such as a silica fiber. For ease of illustration, the absorber and fiber optic are not shown in FIGS. 6A and 6B. In some embodiments, the temperature can be adjusted lower or higher by adjusting the amount of light power delivered to the absorber through the fiber optic.

Figure 7A:
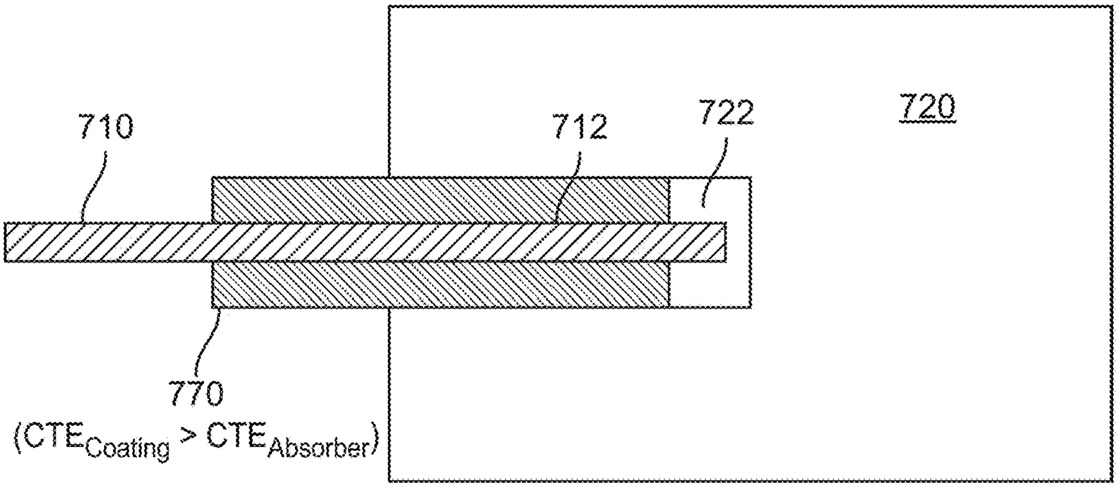
FIGS. 7A and 7B illustrate aspects of photonic treatment or fiber optic probe devices, according to embodiments of the present invention.
Figure 7B:
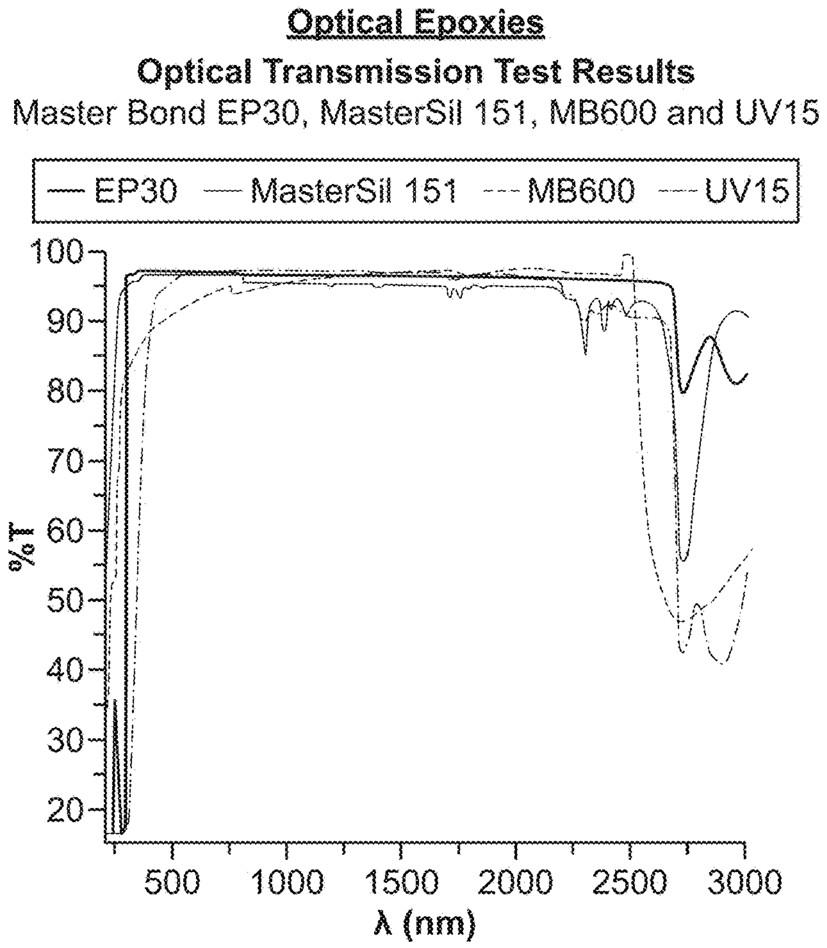

As depicted in FIGS. 7A and 7B, the absorber 720 can be attached to the distal fiber end 712 of the fiber 710 by various means. A mechanical attachment (e.g. clamping, pining, and the like) can be used in coupling the fiber 710 with the absorber 720. In some cases, for example as depicted in FIG. 7A, the absorber 720 can have a small blind aperture 722 etched or drilled into it that is only slightly larger than the fiber 710. The fiber end, close to the light exit, can be coated with a material (e.g. coating material 770) with a larger thermal coefficient of expansion than the absorber (a high temperature acrylate for instance) and press fit into the absorber 720. As the assembly heats up the coated material 770 radially expands faster than the absorber 720, thus making for a tighter fit with temperature increase; frictionally holding the absorber 720 to the fiber 710.

Another means of fixating the absorber to the fiber is through optical epoxies. FIG. 7B depicts optical transmission characteristics of various optical epoxies, according to embodiments of the present invention. Many optical epoxies have very high optical transmissions (>95%) for the wavelength ranges of interest (e.g. 350-2000 nm) and many optical epoxies have high working temperatures. As an example, MasterSil 151 has a workable temperature to over 200° C. and sodium silicate up to 371° C. Ceramic adhesives are another alternative for fixating the absorber to the fiber optic. Ceramic epoxies can handle over 2000° C. and bond to glasses, metals, ceramics, and plastics readily. In the case of gold, another method involves vapor depositing gold onto the end of the fiber and then cold welding the gold absorber to the gold-plated fiber end. In some cases, the absorber can be coupled with the fiber via soldering or brazing.

In some embodiments involving metals, the end of the fiber can be coated with the appropriate metal which can subsequently be brazed or soldered to an absorber of like material or any other material that can be metal coated in a similar manner to the fiber or can be brazed or soldered naturally.

Figure 8:
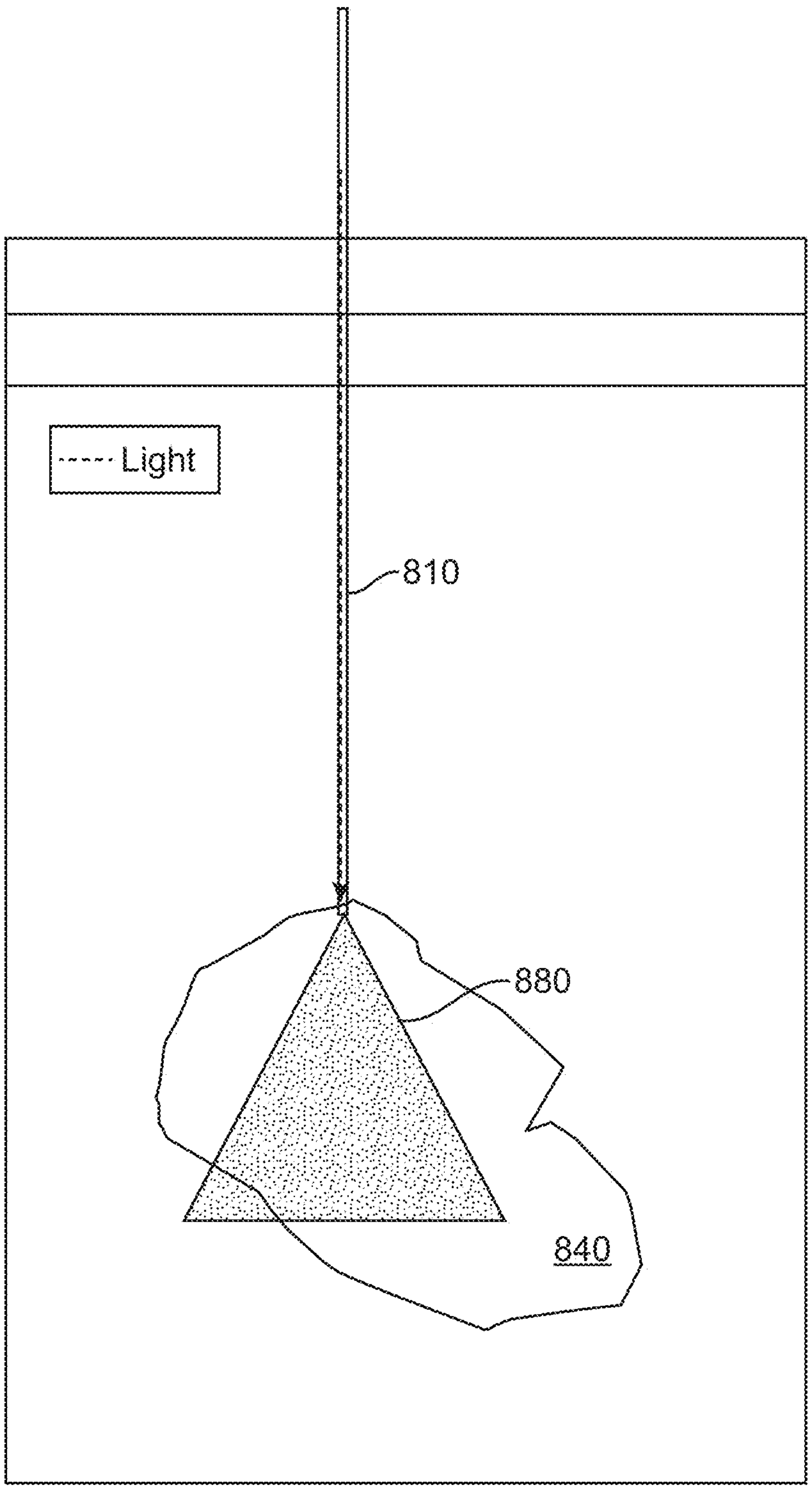
FIG. 8 illustrates aspects of photonic treatment or fiber optic probe devices, according to embodiments of the present invention.

FIG. 8 depicts aspects of a direct illumination method, according to embodiments of the present invention. When light exits the fiber 810, it comes out in a cone shape 880, typically with a Gaussian intensity profile in the far field. The angle of the cone is defined by the numerical aperture (NA) which is defined as the sine of the half angle of the cone.

The NA can be controlled by the launch NA at the proximal end of the fiber and the cladding on the fiber itself. Numerical apertures for standard fused silica fibers can range from 0.10-0.40 which equates to a full cone angle of 10.4 degrees to 47.1 degrees. When exiting into a medium these angles can be smaller due to refraction, for instance these angles in water can be 8.6 degrees to 35.0 degrees. It is possible to adjust the output NA with a fiber to fiber coupler or similar optics at the launch when using a laser of sufficient brightness (i.e. low NA) as the light source.

In some embodiments, delivery of illumination energy can produce its own acoustic sound source through the thermal shock induced by the high intensity light. Such acoustic effects can be used to analyze tissue and/or tissue effects, as described elsewhere herein.

In some cases, the fiber can be cleaved so that the fiber exit face (e.g. at distal end of fiber) is not perpendicular to the fiber axis. This can allow for illumination at non-normal angles to the fiber axis; perhaps to get around an object or to illuminate hard to reach areas that are not accessible straight on.

Wavelengths which can be used span from UV (150 nm) to mid-IR (3000 nm) with each wavelength interacting with the tissue in different ways as different absorption bands of varying molecules and/or atoms are excited, depending on the wavelength of light used. For instance, UV light may kill the tissue like a severe sunburn (causing apoptosis of the cells through DNA damage), while near infrared radiation would 'softly' heat the cells through absorption of the light due to rotational and vibrational excitations of the molecules in the tissue. 'Softly' meaning the atomic bonds of the cells' individual molecules remain intact.

Hence, as shown in FIG. 8, a method of treating a patient presenting with a diseased tissue, for example a cancerous tumor 840, can include placing a fiber optic 810 within the diseased tissue of the patient, and delivering photonic energy to the diseased tissue 840 via the fiber optic. In the embodiment depicted here, the diseased tissue 840 can be considered as a target tissue for treatment.

Table 1 below depicts aspects of a direct illumination method. See also Sandell et al. J. Biophotonics 2011 Nov. 4 (11-12):773-87 (2011), the content of which is incorporated herein by reference, for additional aspects of in vivo optical properties at various treatment wavelengths. As light transverses the tissue, two processes can take place. The first is absorption, which is the process in which the light energy is absorbed by the tissue and converted to heat. An equation describing absorption is:

$$I = I_0 e^{-\mu_a D}$$

where $I_0$ is the starting intensity, $\mu_a$ is the absorption coefficient, and D is the distance into the sample from the source.

TABLE 1

In vivo optical properties at various treatment wavelengths

| Tissue | λ (nm) | $\mu_a$ (cm$^{-1}$) | $\mu_s$' (cm$^{-1}$) | Experimental Method |
|---|---|---|---|---|
| Breast | 660 | 0.037-0.110 | 11.4-13.5 | 1,3 |
| | 760 | 0.031-0.10 | 8.3-12.0 | 1,3 |
| | 900 | 0.096-0.29 | 3.33-5.86 | 1,3 |
| Tumor | 530 | 0.60-0.86 | 28.0-32.1 | 3 |
| | 690 | 0.070-0.10 | 14.7-17.3 | 2 |
| | 895 | 0.068-0.102 | 12.4-13.1 | 2 |

Methods:
1 time of flight absorption spectroscopy
2 frequency resolved spectroscopy
3 continuous wave (CW) absorption reflectance spectroscopy The absorption coefficient, given in inverse units of length, describes how the intensity of the light is attenuated as it passes through the tissue, and thus how much energy is lost in the tissue as heat. This provides for a less localized heat profile than the absorption method described earlier. The absorption coefficient can also be selectively modified by 'staining' or 'dyeing' the tissue to be treated with a photosensitive material that raises the absorption coefficient in the area of interest, thus providing selectivity to the area to be treated.

The second process is scattering in which the light ray is deflected into a different direction than its current (or original) direction. The scattering coefficient us is a measure of the scattering intensity of the material in question. Scattering does not contribute to heating of the tissue directly but will contribute to the heat flux density volumetric profile.

Figure 9:
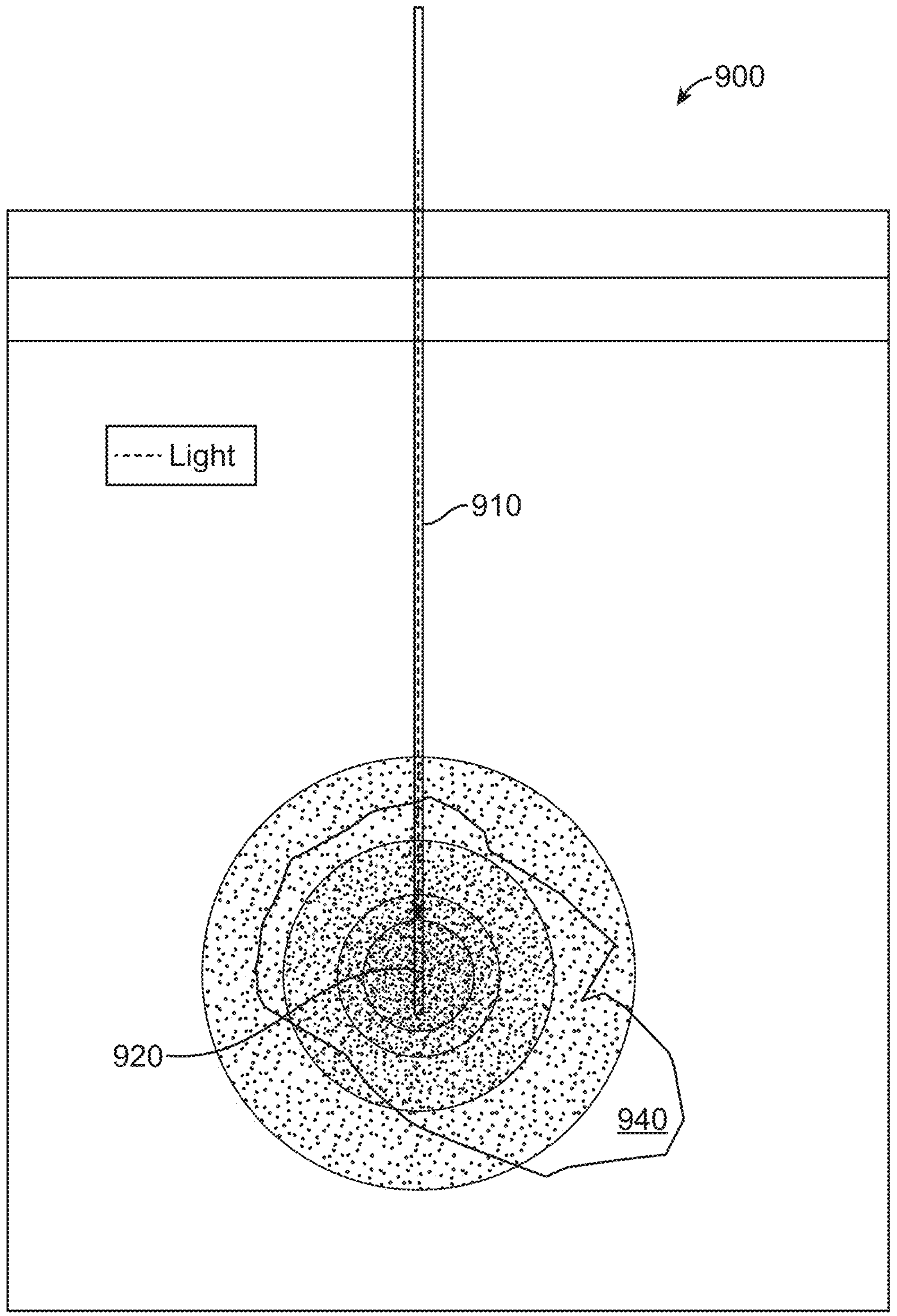
FIG. 9 illustrates aspects of photonic treatment or fiber optic probe devices, according to embodiments of the present invention.

FIG. 9 depicts aspects of a scattering illumination method, according to embodiments of the present invention. A diffuse scatterer 920 can be attached to the end of the fiber 910 and allow the light to scatter isotopically or very nearly isotopically. This allows light to radiate out from the scatterer in a nearly spherical profile, illuminating the surrounding tissue (which includes target tissue 940) in a uniform manner.

As with the direct illumination, the light can be absorbed as it passes through the tissue and converted to heat. This creates a heat flux profile that tapers off as a function of distance from the center of the scatterer. As in the direct illumination technique, the tissue to be treated can be 'stained' or 'dyed' to raise its absorption coefficient and thus add differentiation from the surrounding tissue.

Any number of scatterers can be used, ceramic alumina or zirconia are translucent to most wavelengths that can be used, and they can be manufactured to be highly turbid providing excellent isotropic profiles. Additionally, frosted glass can be employed or the outer surface of the fiber itself can be roughened to provide a scattering zone along a length of the fiber.

Attachment of the scatterer can be similar to the absorber. In some cases, a transparent or translucent resin or epoxy can be used. In some cases, the scatterer may be fused to the fiber directly through a fusion splice process if the scatterer material is compatible with the fiber material. The joint can be capable of passing light, be it transparent or translucent.

Hence, as shown in FIG. 9, a method of treating a patient presenting with a diseased tissue 940, for example a cancerous tumor, can include placing a fiber optic 910 of a device 900 within the diseased tissue 940 of the patient, and delivering photonic energy to the diseased tissue via the fiber optic 910. In some instances, the fiber optic 910 is coupled with an absorber mechanism 920. In some instances, the fiber optic is coupled with a scatterer mechanism 920. In the embodiment depicted here, the diseased tissue 940 can be considered as a target tissue for treatment.

Figure 10B:
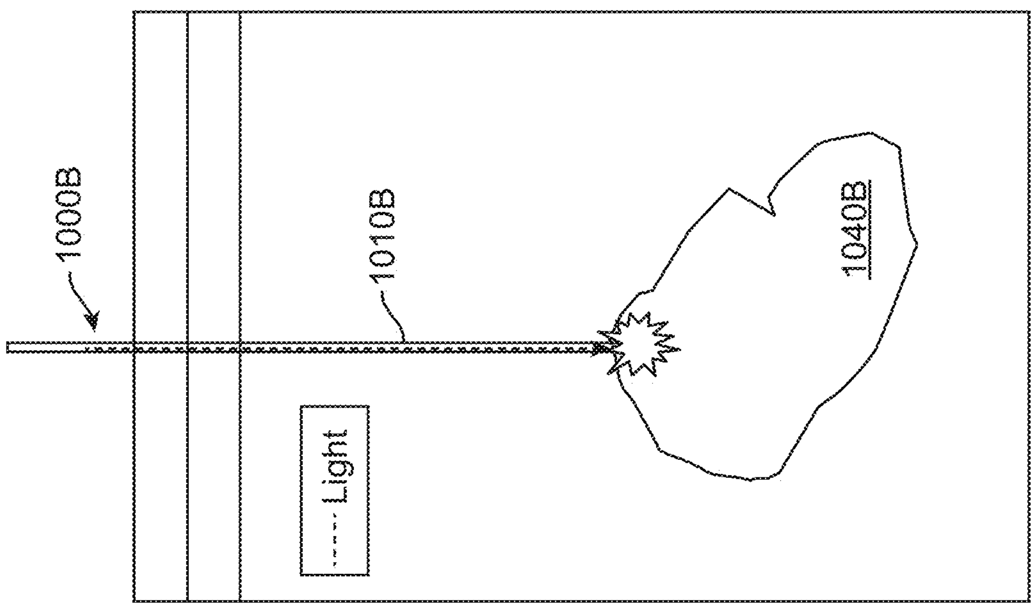
FIGS. 10A and 10B illustrate aspects of photonic treatment or fiber optic probe devices, according to embodiments of the present invention
Figure 10A:
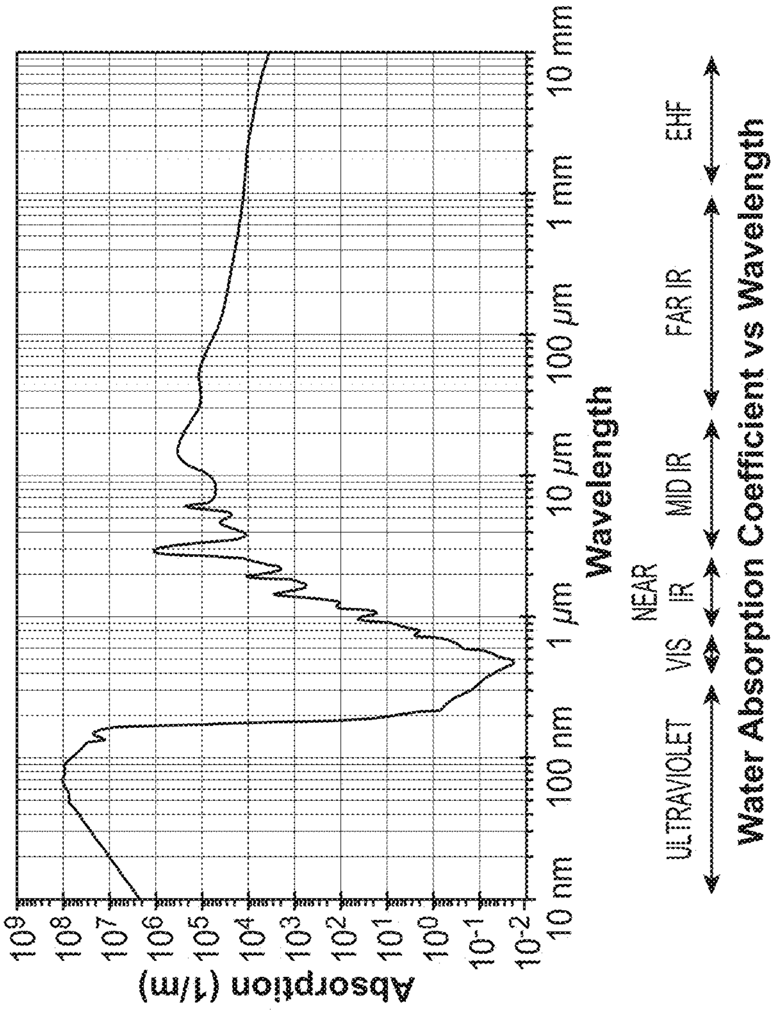

FIGS. 10A and 10B depict aspects of ablation/vaporization methods, according to embodiments of the present invention. In some cases, such techniques can be similar to the direct illumination method, but with very short, high intensity light pulses. When the wavelength is sufficiently long or short (deep UV), the absorption coefficient becomes very large. This means the majority of light energy is absorbed in a very short distance. For instance, in water using a 1500 nm light source, 90% of the light energy will be absorbed within 1.3 mm.

In some embodiments, the ablation and/or vaporization techniques disclosed herein do not involve the heating, charring, and/or dissolving of tissue or other anatomical structures. Exemplary embodiments disclosed herein encompass the vaporization of tissue or other anatomical structures using fiber optics that are a few hundred microns in diameter, by sending high energy pulses down the fiber optics capable of vaporizing material at the end of the fiber, without requiring the use of large bulky optics (e.g. collimating and refocusing optics).

Q-switched lasers can produce very high-power short pulses and can be provided in a variety of wavelengths. The high concentration of energy combined with the short transient times can result in an adiabatic thermal reaction in which the heat cannot conduct away from the affected zone in time, thus causing the tissue material in a small volume to become superheated resulting in ablation or vaporization of the tissue.

Hence, as shown in FIG. 10B, a method of treating a patient presenting with a diseased tissue 1040B, for example a cancerous tumor, can include placing a fiber optic 1010B of a device 1000B within the diseased tissue of the patient, and delivering photonic energy to the diseased tissue via the fiber optic 1010. In the embodiment depicted here, the diseased tissue 1040B can be considered as a target tissue for treatment.

As an example, a 2000 nm wavelength laser with a 35 ns width pulse can deposit 520 mJ of energy per pulse which can heat the illuminated tissue up to 47,000° C. in the duration of the 35 ns pulse (e.g., see simulation results depicted in FIGS. 11A-11D). This is many times hotter than the surface of the sun. The tissue would vaporize before ever reaching this temperature. As a second example, a 1500 nm laser with a 50 ns pulse that can deposit 80 mJ of energy was also simulated. 1500 nm light has a lower absorption coefficient than 2000 nm light (1800 $m^{-1}$ vs 10000 $m^{-1}$ in water), so spreads the heat through a larger volume. This will reduce the peak temperature, however at a temperature over 1400° C. (2552° F.), the tissue can be destroyed within the 50 ns pulse, though may not create a plasma vapor as can be the case in the 2000 nm light source.

The absorption of water can be used as a first approximation for determining the absorption coefficients of human tissue at 2000 nm or 1500 nm. Furthermore, since the beam is quickly absorbed close to the fiber, the beam is assumed to maintain its near field intensity profile (i.e. closer to radially uniform than radially Gaussian).

The intensity of the light pulse may be extremely large which can result in non-linear effects in the fiber. Thus, it may be desirable to use hollow core fibers, photonic band gap fibers, or other fiber designs that have non-linear mitigation features. Additionally, the end of the fiber may be protected with a high temperature transparent ceramic such as alumina or other transparent high temperature material.

Many Q switched lasers can operate in the kilohertz range, so while the amount of tissue volume destroyed per pulse may be small, the overall tissue volume removal rate can be significant.

Additionally, when a pulse hits the tissue there can be a thermal shock that creates a pressure wave (acoustical) that can be detected and used for imaging or other diagnostic purposes.

According to some embodiments, it is possible to apply external optics to expand and refocus the beam to a power density capable of material/tissue vaporization with lower pulse energy.

Figure 11A:
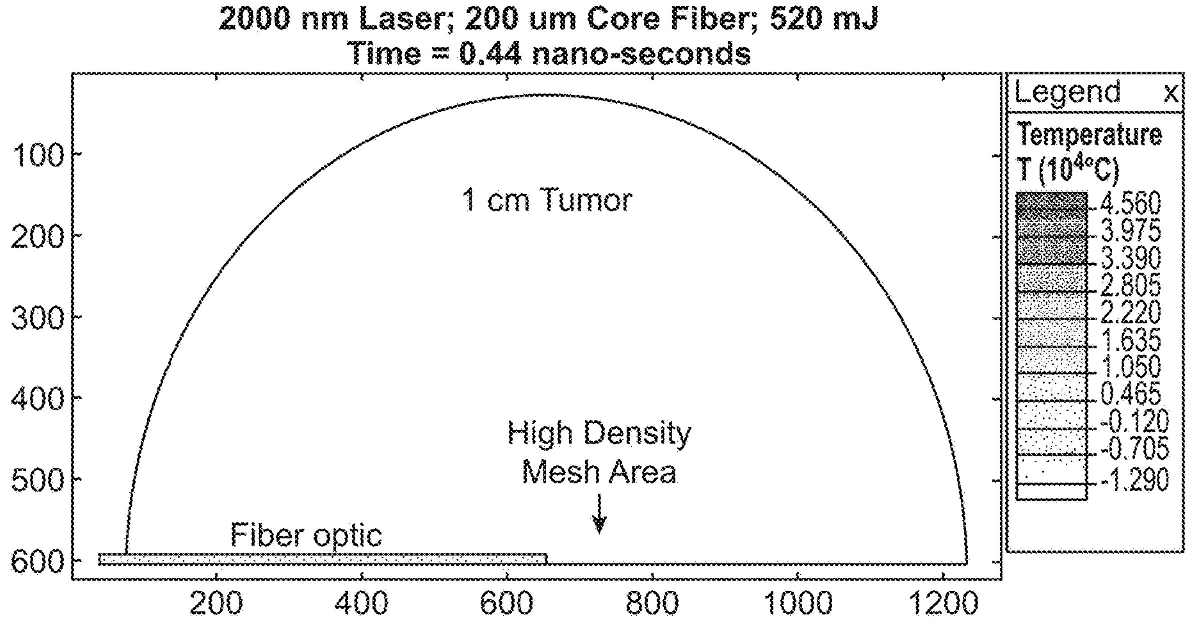
FIGS. 11A to 11D depict aspects of photonic treatment methods, according to embodiments of the present invention.
Figure 11B:
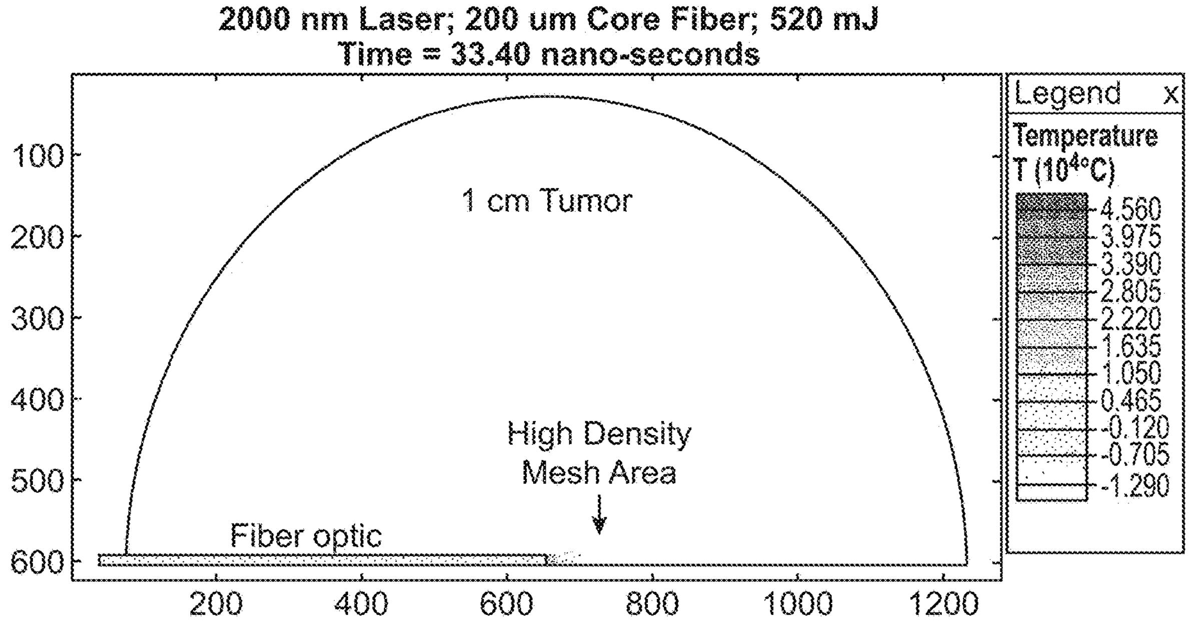

As depicted in FIGS. 11A and 11B, embodiments can encompass the use of a 2000 nm laser (35 nS Pulse, 520 mJ of Energy per pulse) with a 200 micron core fiber optic (0.1 NA) and the simulated maximum temperature reached is ~47,000° C.

Figure 11C:
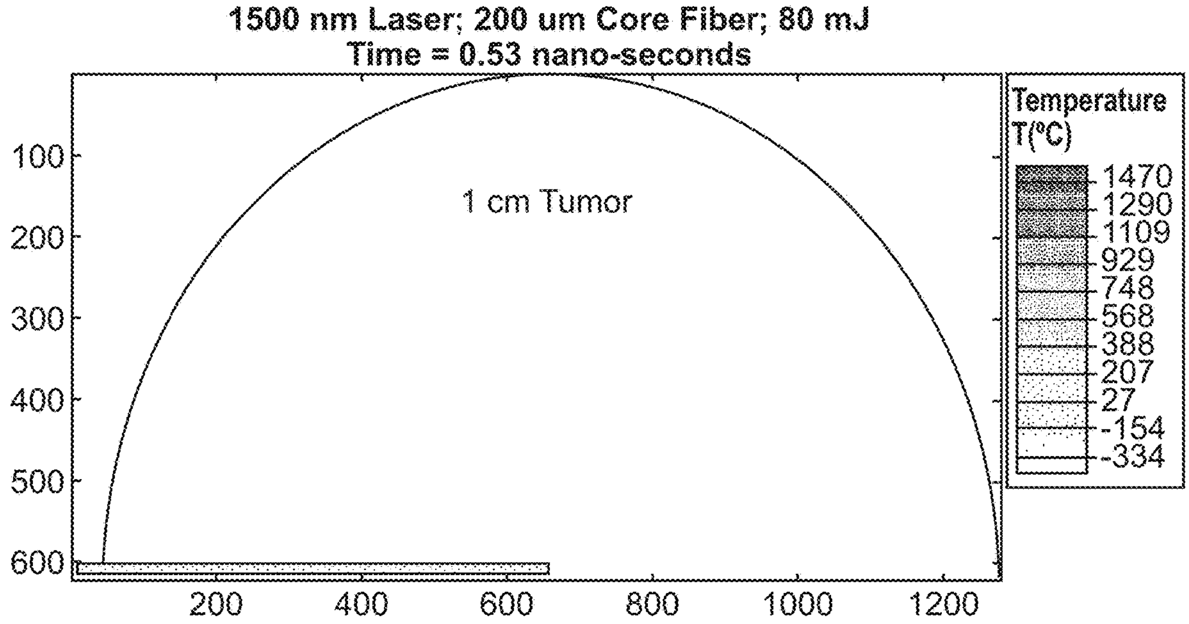
Figure 11D:
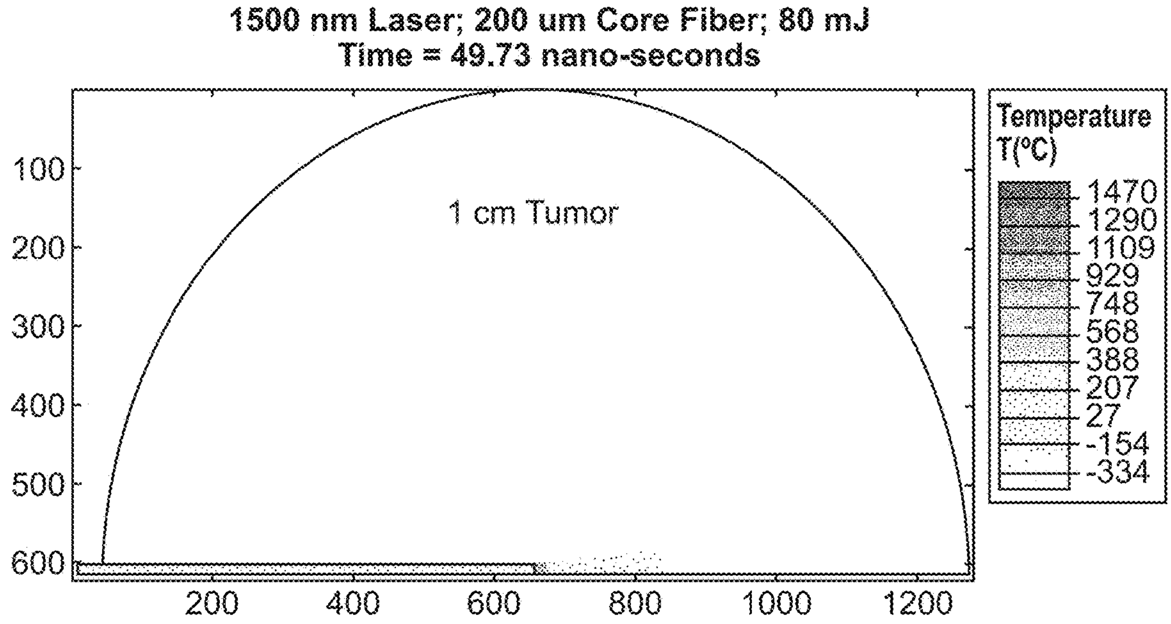

As depicted in FIGS. 11C and 11D, embodiments can encompass the use of a 1500 nm laser (50 nS Pulse, 80 mJ of Energy per pulse) with a 200 micron core fiber optic (0.1 NA) and the simulated maximum temperature reached is ~1,400° C.

A high-density finite element simulation mesh volume can accurately model the heating of the tissue in the region of interest in the finite element transient analyses performed.

Figure 12A:
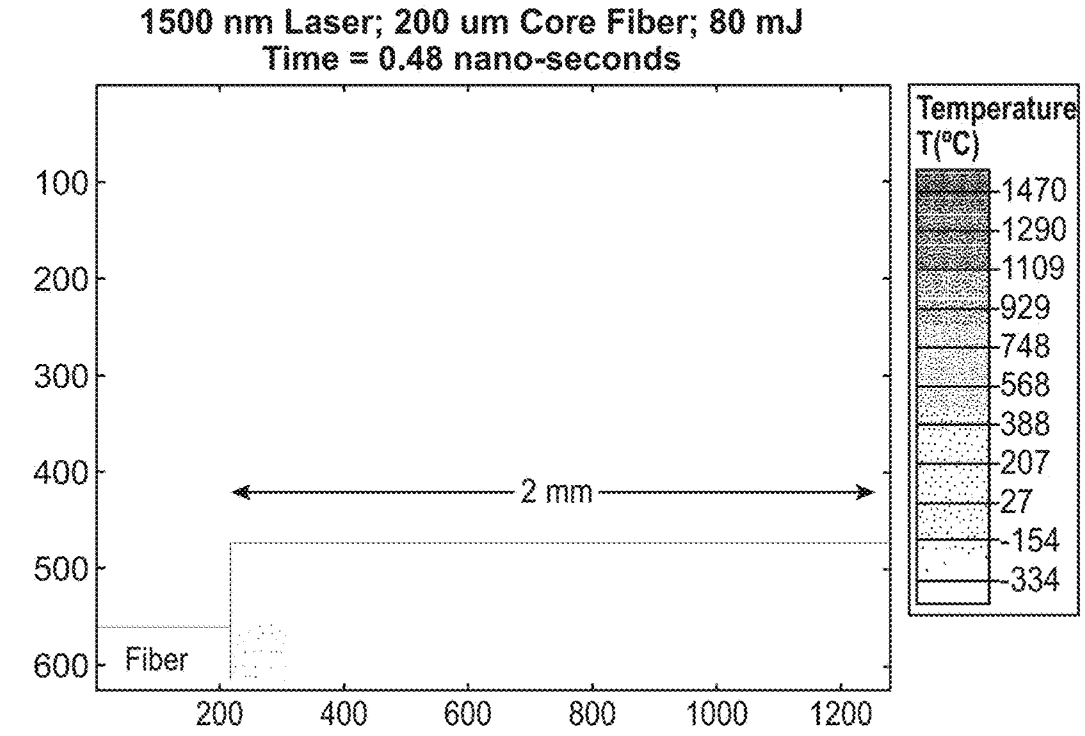
FIGS. 12A to 12D depict aspects of photonic treatment methods, according to embodiments of the present invention.
Figure 12B:
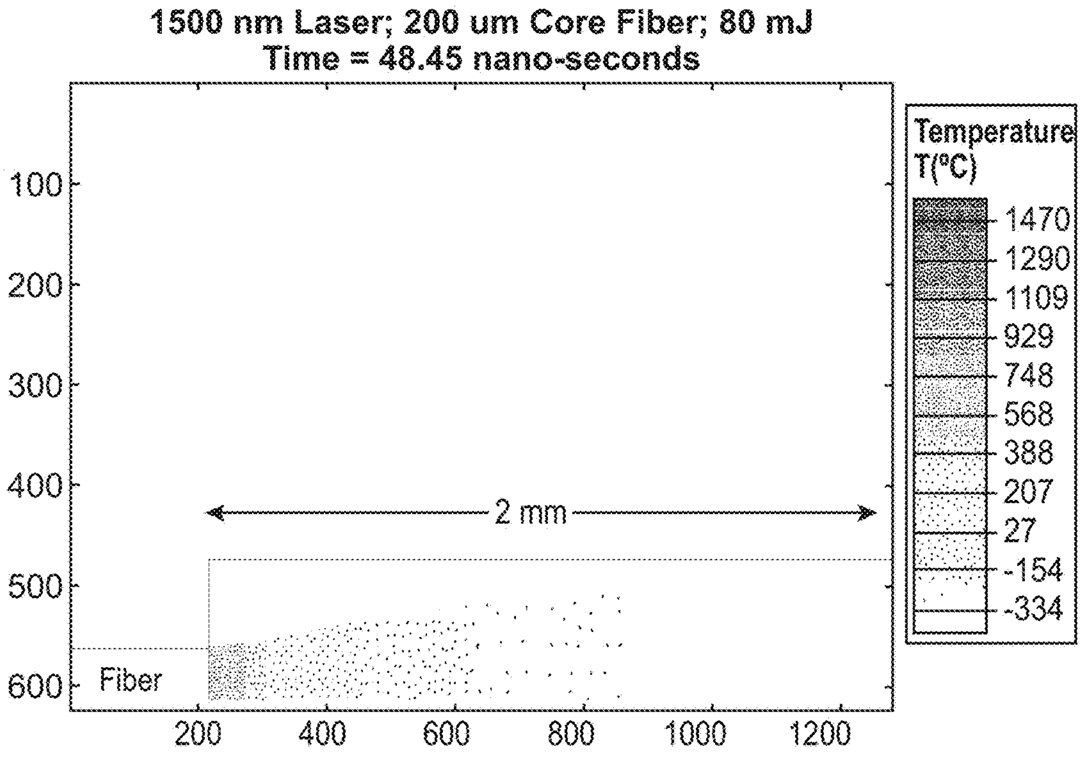

As depicted in FIGS. 12A and 12B, an ablation/vaporization simulation (zoomed to region of interest) can involve a 2000 nm laser, and the simulated maximum temperature reached is ~47,000° C.

Figure 12C:
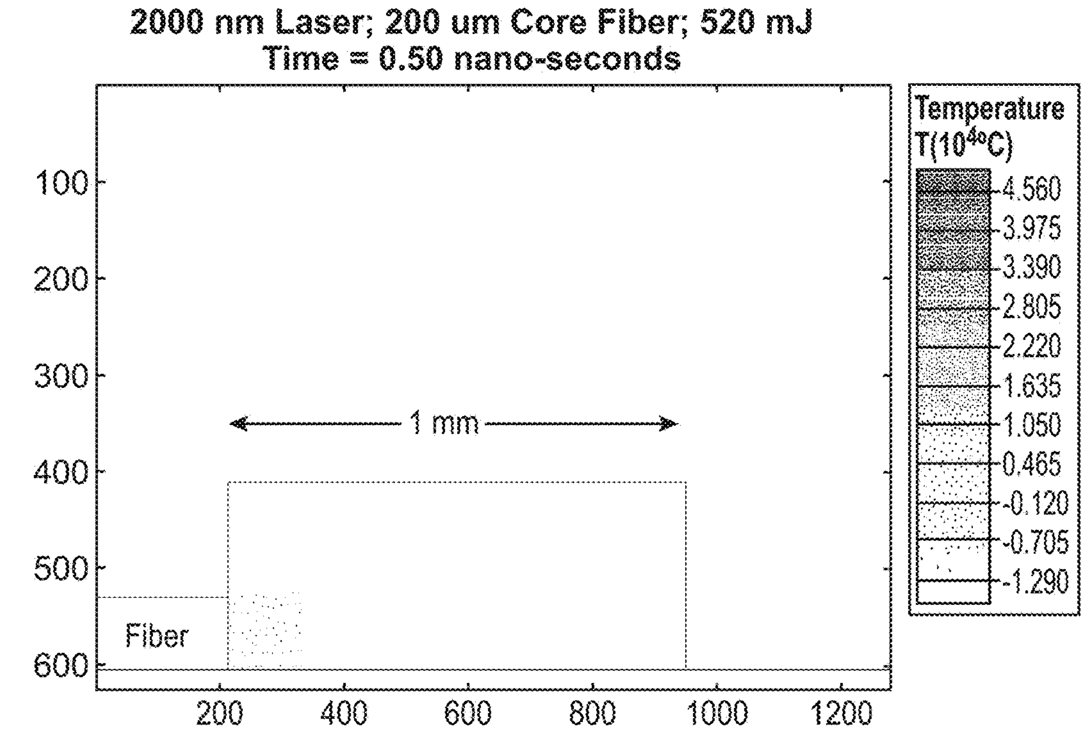
Figure 12D:
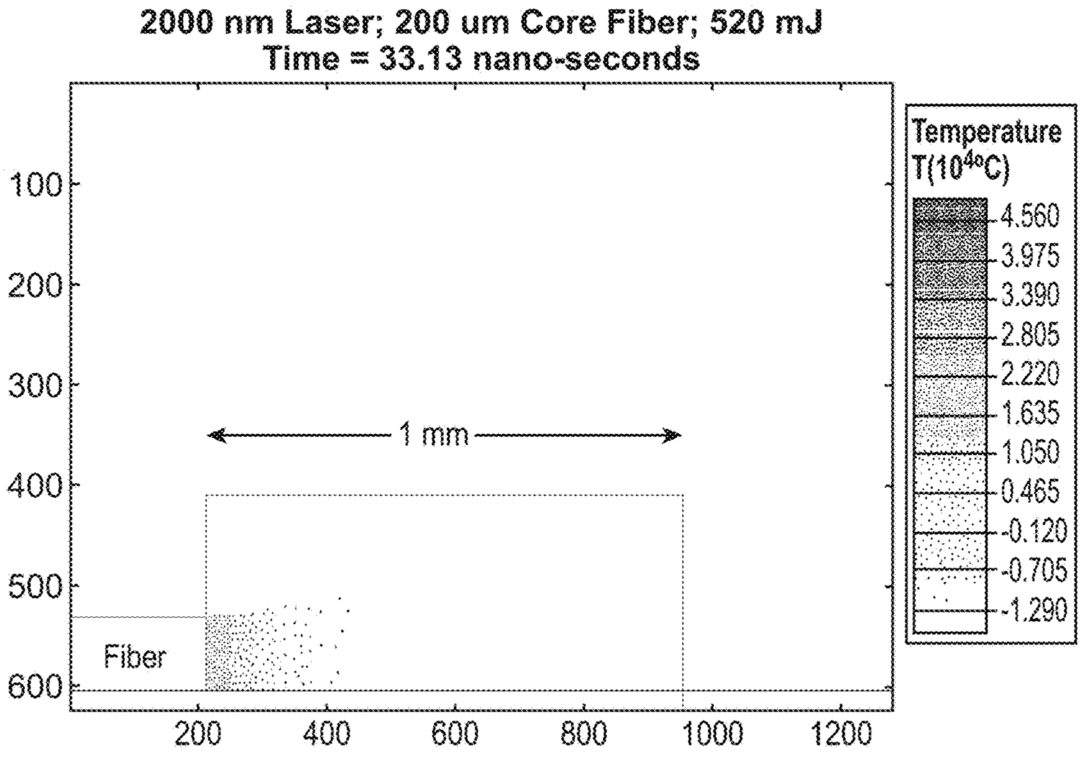

As depicted in FIGS. 12C and 12D, an ablation/vaporization simulation (zoomed to region of interest) can involve a 1500 nm laser, and the simulated maximum temperature reached is ~1,400° C.

Hence, exemplary methods can involve the use of a desired wavelength of light (e.g. 1400-2000 nm, deep UV, and the like) such that the absorption is high (>90% absorbed in less than a few millimeters) in the tissue with a very short high intensity pulse of light. If the energy absorption takes place in much less time than the thermal relaxation of the tissue, nearly all of the energy deposited can go into heating the tissue in the absorption volume causing the tissue to reach extreme temperatures within the pulse (thousands or tens of thousands of degrees Celsius), ablating or vaporizing the tissue in that small volume. In some embodiments, vaporization means the tissue is reduced to a gaseous or even plasmatic state (plasma being ionized gas, not blood plasma). In some embodiments, vaporization means the treated tissue or material reaches extremely high temperatures, where molecules are obliterated, and the atoms are potentially turned to plasma or at a minimum turned to a nearly gaseous state instantaneously. Char and burned material are not left behind in such a vaporization process, and the tissue appears to vanish in an instantaneous bright flash, not slowly simmer. In some cases, vaporization means the tissue or treated structure is treated with temperatures up to tens of thousands of degrees Celsius, and hence are much higher than a temperature within a range from 40 to 45° C. where necrosis of the cell takes place.

Figure 13:
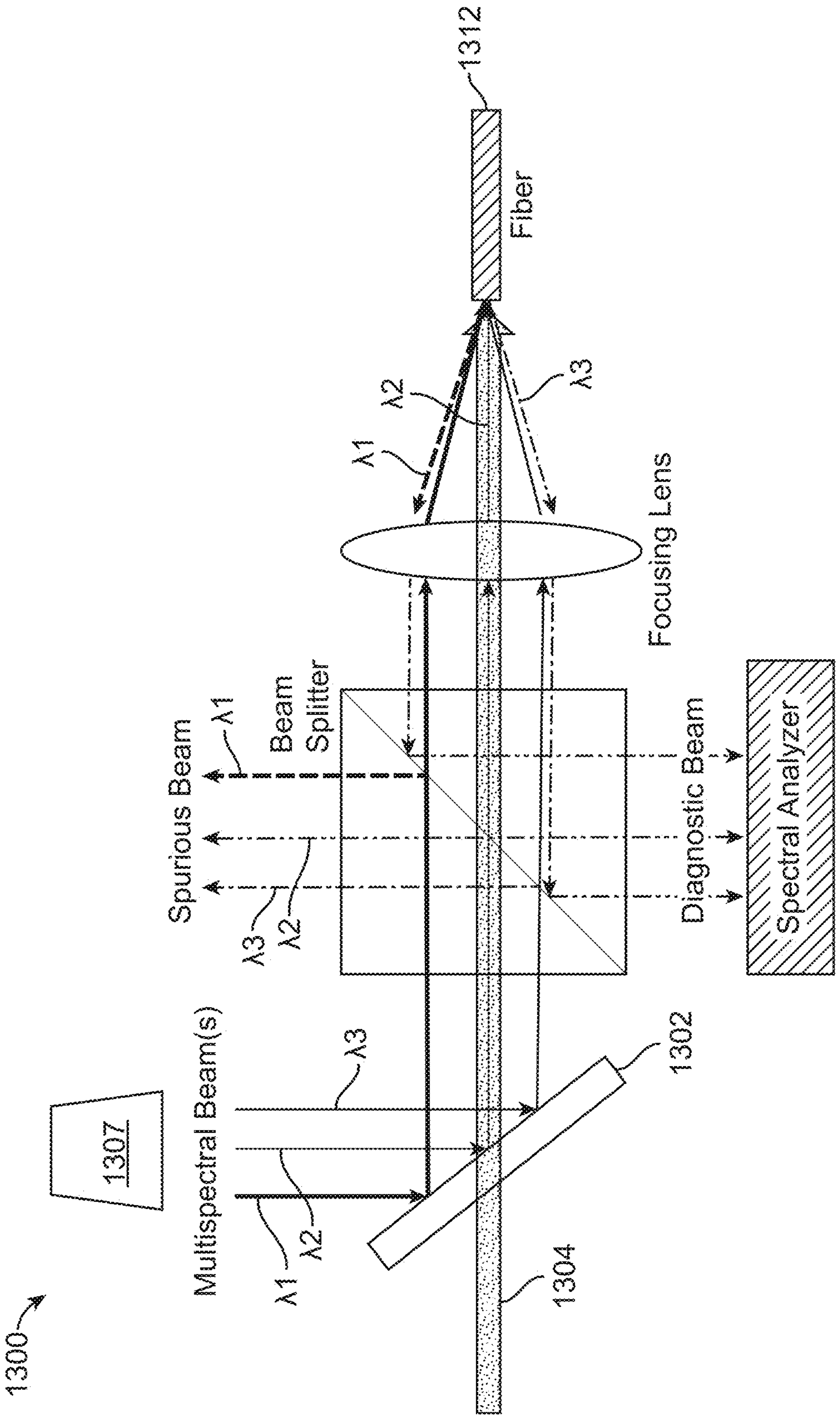
FIG. 13 depicts aspects of photonic treatment and/or diagnostic methods, according to embodiments of the present invention.

FIG. 13 depicts aspects of a diagnostic technique, according to embodiments of the present invention. Because some light may be scattered from the surrounding tissue, a small amount may make its way back up the fiber optic where is can be used as a diagnostic. This may include measuring reflected light intensity, spectral profiling, Raman spectroscopy, fluorescence, or any other light-based diagnostic available to the artisan. This may allow for detecting which type of tissue the probe is currently in and the condition of the tissue during treatment. One advantage to using a photonic hyperthermia treatment is the feedback possible from light scattered from the tissue or produced in an ablation/vaporization process. This data can be used for diagnostic purposes prior to the treatment, during the treatment, and after the treatment. Measures such as intensity fluctuations, spectral response, and Raman spectroscopy can be used to infer data about the tissue and treatment process in real time or posthumously.

As shown in FIG. 13, a system 1300 capable of implementing diagnostic techniques can include of a notch filter 1302 that transmits the main (working) beam 1304 and reflects other wavelengths (e.g. Λ1, Λ2, and Λ3). The system also contains a 50/50 beamsplitter (other split values are possible) that transmits the main beam 1304 and reflects the multispectral beam (e.g. λ1, λ2, and λ3). The main beam 1304 and the multispectral beam (e.g. Λ1, Λ2, and Λ3) are focused into the fiber using a focusing lens. A broadband light source 1307 such as a lamp or a number of lasers of different wavelengths can be used to create the multispectral beam. A portion of the multispectral beam can be reflected at the beam splitter before being launched into the fiber, here called the spurious beam. As depicted here, the spurious beam does not pass through the lens. Rather, it is reflected off the beam splitter before reaching the lens. Hence, the spurious beam light does not travel through the lens or the fiber. This light may be used for baseline stability or other comparative measures. The amount of light reflected into the spurious beam may be controlled by the beamsplitter coating design. The diagnostic beam intensity can be highly correlated to the beamsplitter design in the case of unpolarized light. Multispectral light that is reflected/scattered from the tissue and makes its way back up the fiber (e.g. entering distal end 1312 of the fiber) can be reflected at the beam splitter and enter into a spectral analyzer for analysis. In some cases, the multispectral techniques as described herein can be carried out instead with a single wavelength. For example, single wavelength embodiments can utilize Raman spectroscopy analysis.

Different tissues will have different absorption and scatter characteristics as a function of wavelength, thus spectral profiles may provide fingerprints of the tissue that is being irradiated. Furthermore, the characteristics of the tissue may change as the hyperthermia or ablation treatment proceeds giving informative feedback on the process in real time. Additionally, Stokes shifts in the wavelengths (i.e. Raman scattering) may be detected in the main beam and/or the multispectral beam if the multispectral beam is composed of multiple individual wavelengths. Regarding Raman scattering, when certain molecules/materials scatter light, sometimes a portion of the photon energy goes into exciting rotational or vibrational states in the molecules or phonons in the material. A portion of the photon energy can be given up to the molecule or material and can subsequently produce a distinct wavelength shift for a given molecule or material. This wavelength shift can be used to accurately identify molecules and materials. The difference in wavelength between the incoming photon and the scattered photon can be referred to as the Stokes shift.

Additionally, if the main beam and multispectral beam are linearly polarized, they can pass through the beamsplitter with only a very small amount of power being diverted into the spurious beam. The scattered light that returns back up the fiber can be unpolarized and can reflect strongly into the diagnostic beam subject to the beamsplitter design. In some embodiments, if desired, some portion of the main beam can also be reflected into the spurious beam and can appear in the diagnostic beam, from backscatter from the tissue, as well. The beamsplitter can be designed to minimize this, however the additional diagnostic data from the main, presumably more intense, beam may be useful.

Figure 14A:
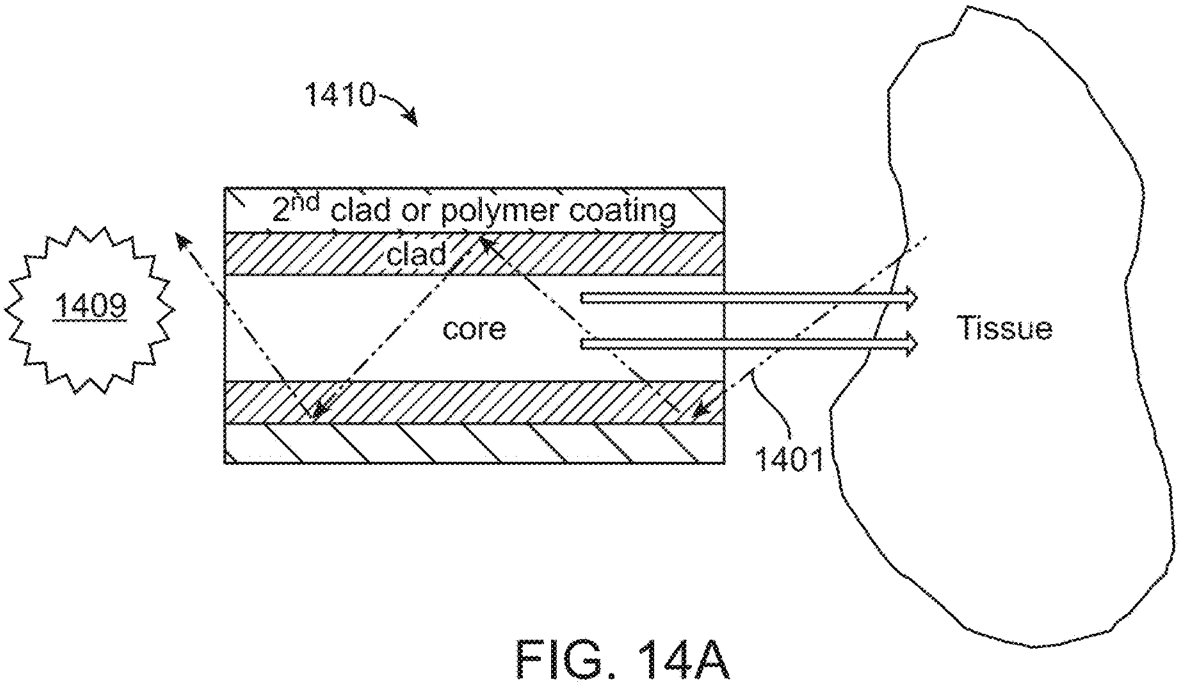
FIGS. 14A and 14B depict aspects of photonic treatment and/or diagnostic methods, according to embodiments of the present invention.
Figure 14B:
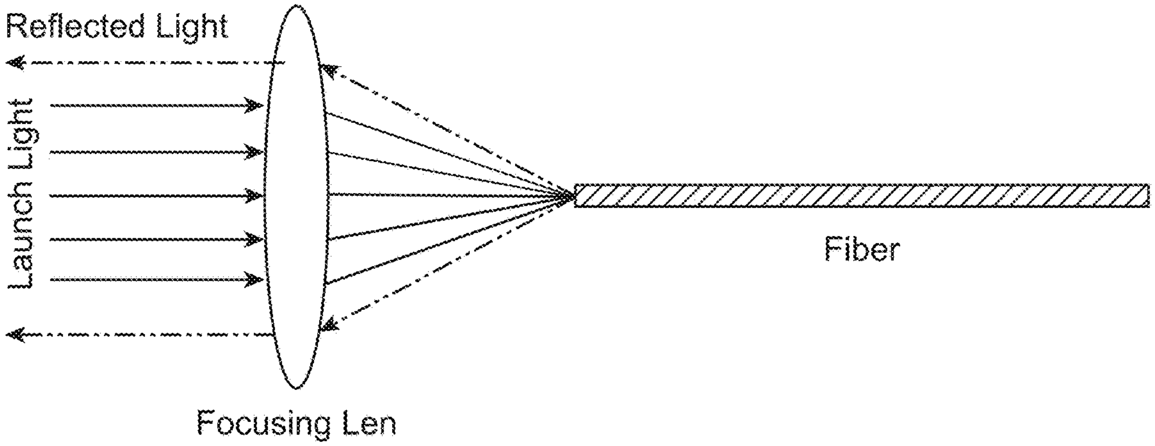

As depicted in FIGS. 14A and 14B, light traveling down the fiber 1410 from the light source 1409, which may be referred to as the working light, can be completely contained in the core of the fiber. Light 1401 that is scattered and/or reflected from the tissue can enter the clad of the fiber at higher angles than the working light. A second clad or polymer coating can be included on the fiber to prevent leakage of light from the fiber on the back trip. This light can propagate back up the fiber where it can be separated. The separation can be done based on the principle that some of the light 1401 that is reflected back can travel in the clad which allows for larger angles of propagation than the core. Hence, it is understood that fiber 1410 can include one or more clads. As shown in FIG. 14B, the reflected light can be at a larger radius on the lens (e.g. focusing lens) used to focus the light into the fiber at the light source and can be spatially separated there. Alternatively, the light can be rerouted or detected prior to the focusing lens by placing a detector or other optical element (e.g. prism, mirror, or light guide) to spatially separate it from the main beam.

Figure 15A:
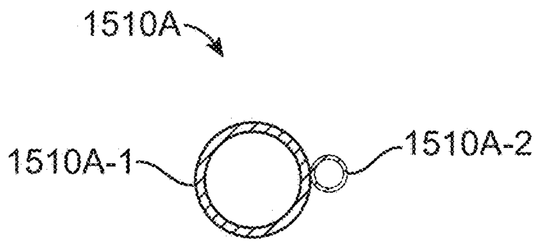
FIGS. 15A to 15C depict aspects of photonic treatment and/or diagnostic methods, according to embodiments of the present invention.
Figure 15B:
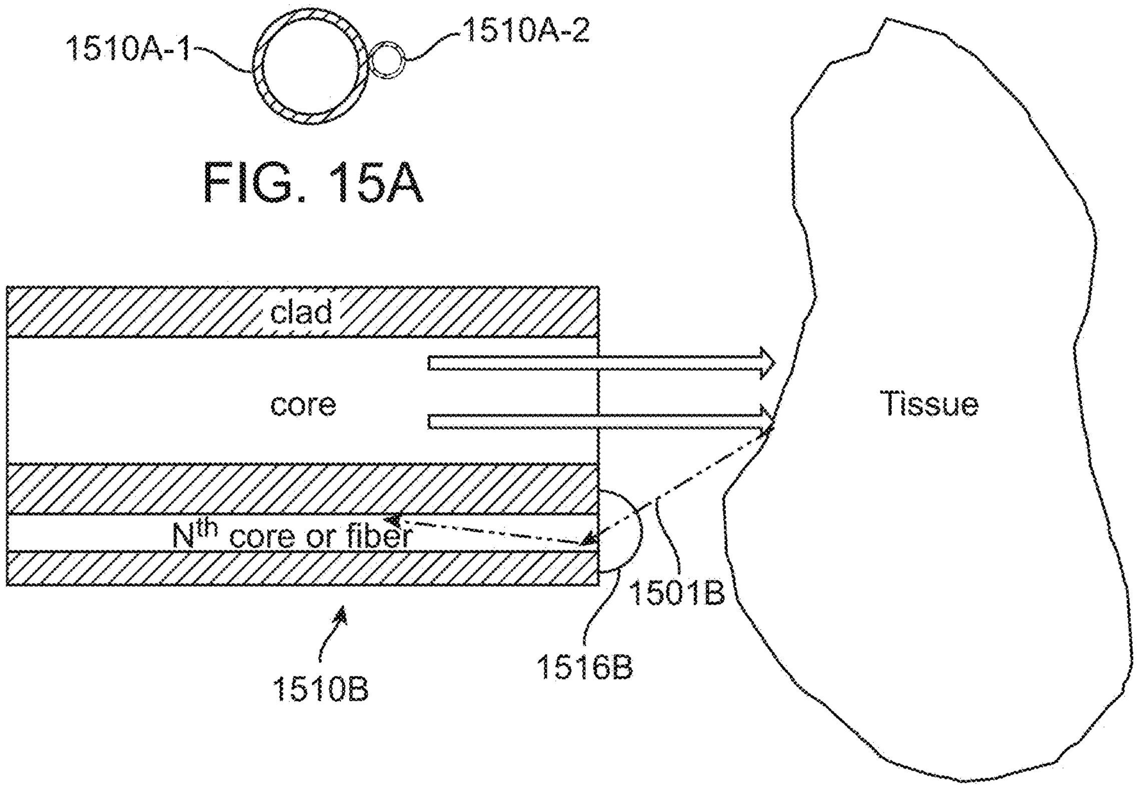
Figure 15C:
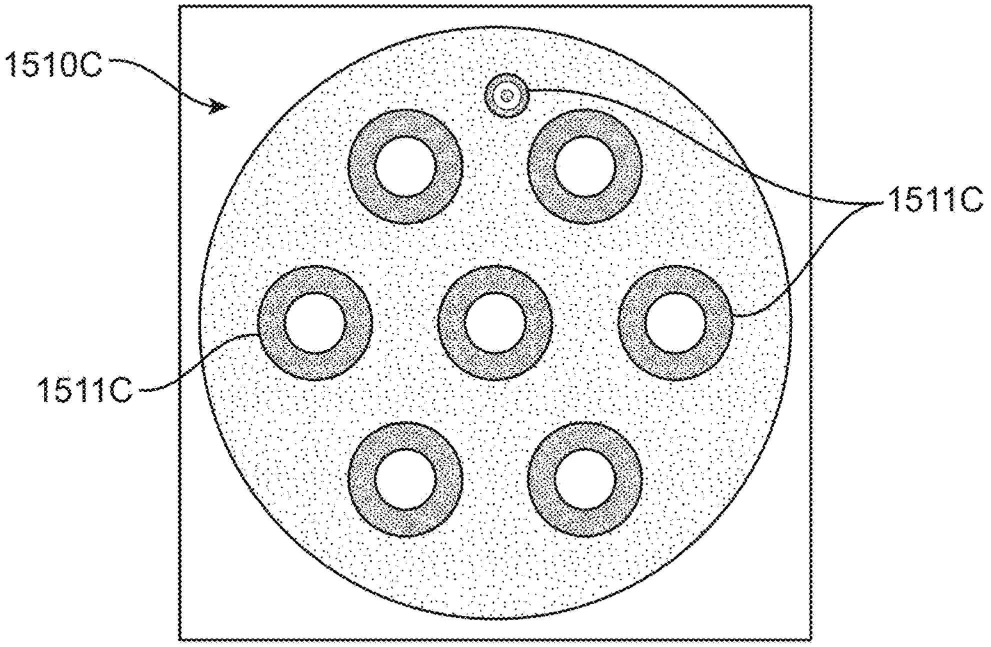

FIGS. 15A-15C depict aspects of multi-fiber systems, according to embodiments of the present invention. FIG. 15A shows a front view of a two fiber system 1510A having a first larger diameter fiber 1510A-1 and a second smaller diameter fiber 1510A-2. Fiber optics such as fiber 1510A can be made very small in diameter, and it is possible to have a second fiber (e.g. 1510-2) fixed to the working fiber (e.g. 1510A-1) for the purposes of diagnostics. The diagnostic fiber can be smaller or larger depending on the application goals and may contain micro-optics to more efficiently collect scattered light. Alternatively, special fibers can be manufactured that have more than one core; one or more cores being used to deliver the energy and one or more cores used to collect scattered light for diagnostics. In some embodiments, such fibers can be referred to as multicore fibers.

According to some embodiments, a small diameter fiber may run in tandem with the power delivering fiber. The tandem fiber can also deliver (or be the primary means of delivering) diagnostic data back to the operator or machine algorithm as the case may be. In the case of vaporization or ablation, the tissue itself can re-radiate light created in the ablation or vaporization process and that light can be captured and spectrally analyzed to identify the tissue as well as other potential diagnostics related to the tissue and its contents. As shown in FIG. 15B, a fiber system 1510B can have cladding and core components, and one or more micro-optic elements 1516B (e.g. at a distal end of a core or fiber). In some cases, reflected light 1501B can pass through a micro-optic element 1516B. FIG. 16C depicts a fiber system 1510C having multiple cores or fibers 1511C.

Figure 16:
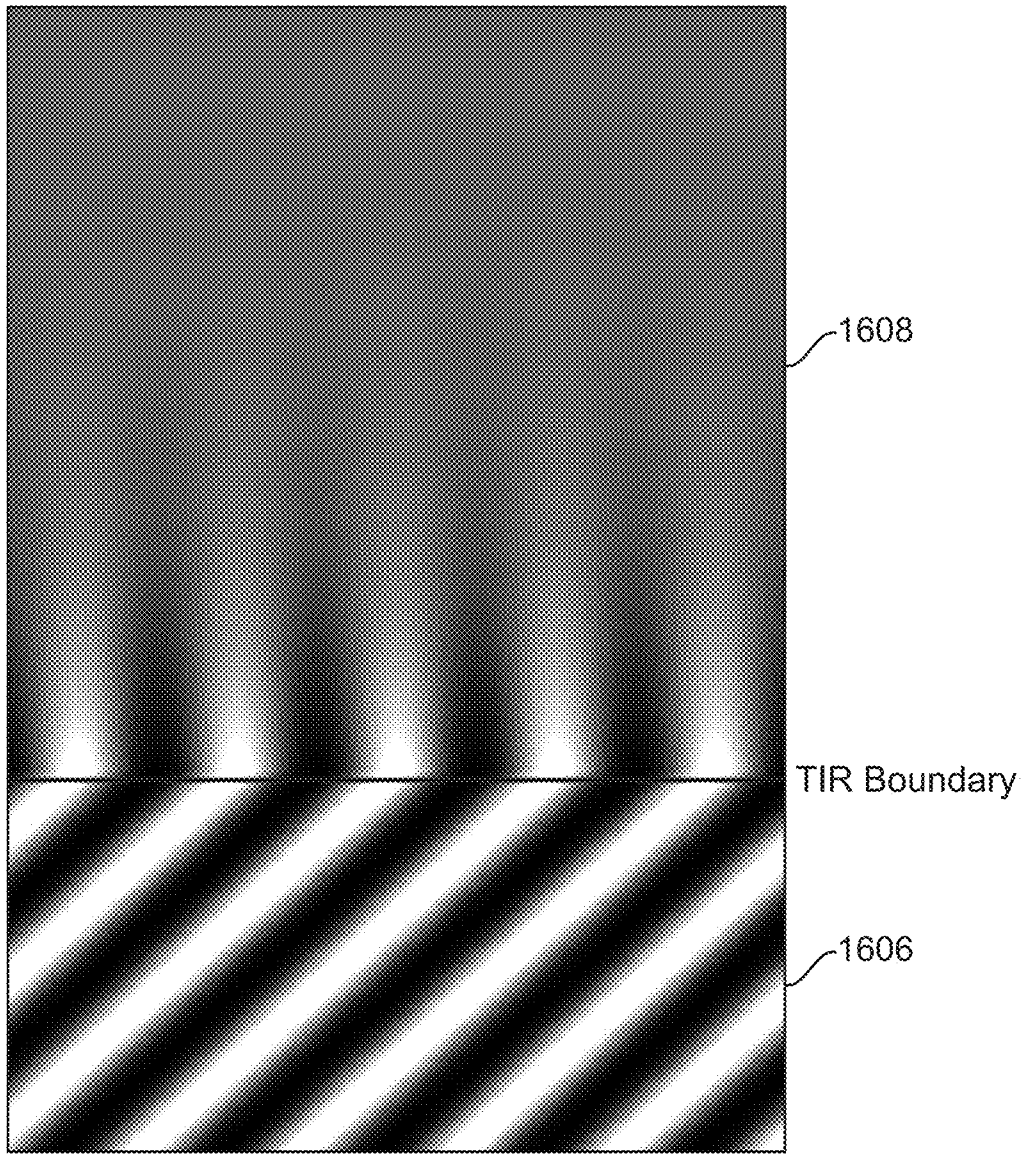
FIG. 16 depicts aspects of photonic treatment and/or diagnostic methods, according to embodiments of the present invention.

FIG. 16 depicts aspects of evanescent coupling heating techniques, according to embodiments of the present invention. As shown here, fiber optics can work by total internal reflection (TIR). Typically, a core 1606 of one refractive index is surrounded by a material of a lower refractive index called the clad 1608. This arrangement allows for total internal reflection of light rays inside the fiber and keeps the light rays confined inside the fiber.

When total internal reflection takes place, the electromagnetic field of the incident wave can extend past the TIR boundary by a few wavelengths (e.g. the total penetration depth outside the boundary depends on the incident angle of the reflected light).

FIG. 16 illustrates the electric field strength at a TIR boundary for an electromagnetic wave (e.g. light). It can be seen that the electric field extends past the boundary on the order of wavelengths. If the evanescent field encounters an object such as a cell or other material it can couple its energy into the object. If this object is absorptive then that energy can be converted to heat. If the wavelength is chosen such that tissue is absorptive, heat can be generated in the tissue. It is also possible to coat the clad in an absorbing material and use that material as the heating element.

According to some embodiments, a second clad can be introduced around the first clad, such that the evanescent field is contained wholly in the second clad and does not come into contact with outside material until heating is desired. At this point the second clad is absent and the evanescent field is allowed to couple into any material or objects it may come into contact with. This may assume the first clad is thin enough that some portion of the evanescent field reaches the outer boundary of the first clad.

In some embodiments, draining of energy from the main field (beam) through the evanescent field into an object is not sudden or instantaneous. The main beam can continue to propagate down the fiber as its energy is drained into the object or objects to be heated. This can allow for a distributed heating along the length of the exposed fiber (exposed meaning the second clad is absent or substantially thin). The rate at which light energy is deposited into the surroundings along the length of the exposed fiber can be controlled by the thickness of the first clad.

Figure 17A:
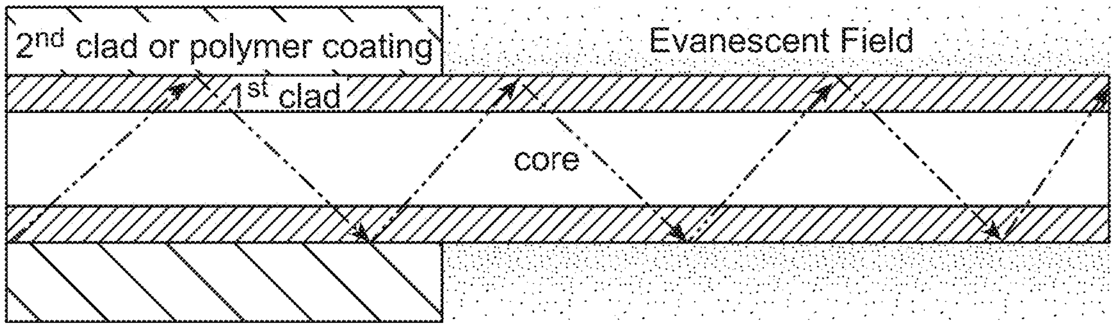
FIGS. 17A and 17B depict aspects of photonic treatment and/or diagnostic methods, according to embodiments of the present invention.
Figure 17B:
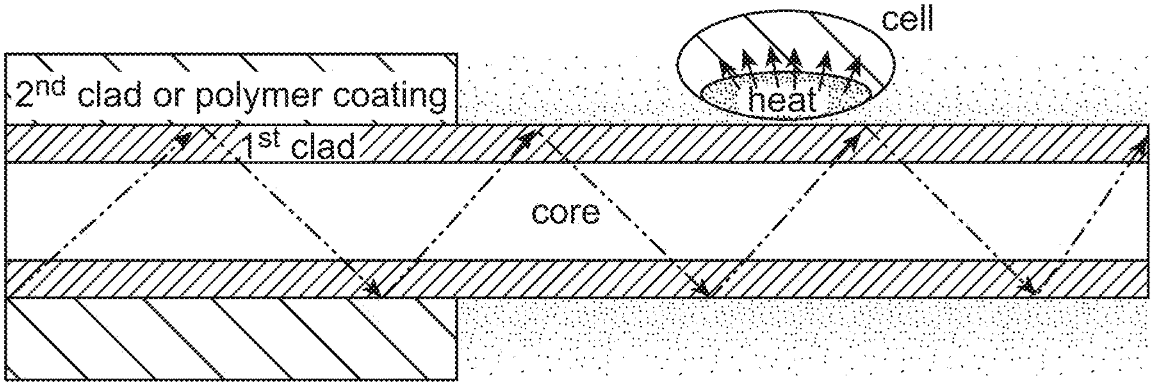

FIGS. 17A and 17B depict aspects of evanescent coupling to tissue, according to embodiments of the present invention. As shown in FIG. 17B, if the evanescent field encounters an object such as a cell or other material it can couple its energy into the object. If this object is absorptive then that energy can be converted to heat. For example, the fiber optic can include a core, a first clad, and a second clad. The first clad can be disposed peripherally to the core, the second clad can be disposed peripherally to a covered portion of the first clad, and an evanescent electromagnetic field extending past a total internal reflection boundary of the first clad can be contained in the second clad where the second clad is disposed peripherally to the covered portion of the first clad, and can generate heat in absorptive tissue (e.g. one or more cells) near the fiber optic at a location near an uncovered portion of the first clad that is adjacent to the covered portion of the first clad. In this sense, the heat can be generated where there is no second clad.

Figure 18A:
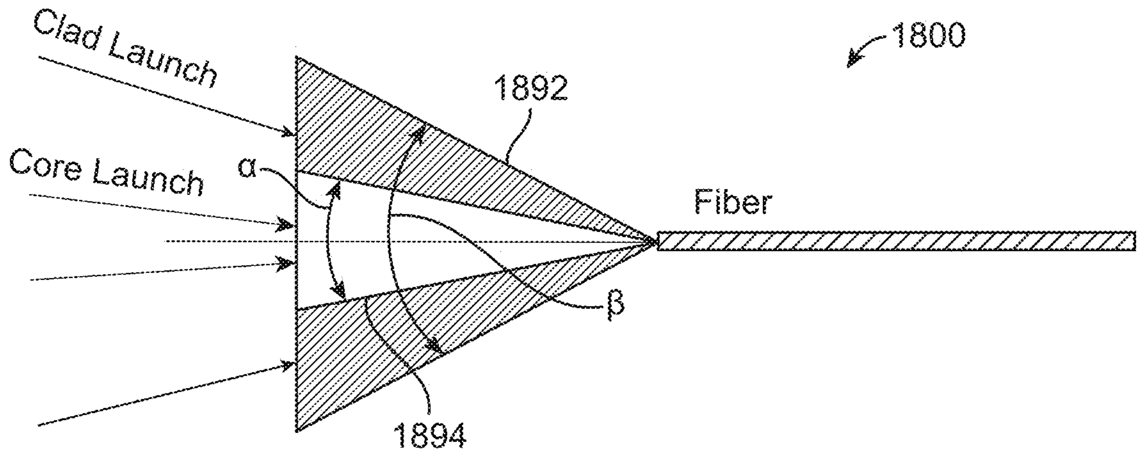
FIGS. 18A and 18B depict aspects of photonic treatment and/or diagnostic methods, according to embodiments of the present invention.
Figure 18B:
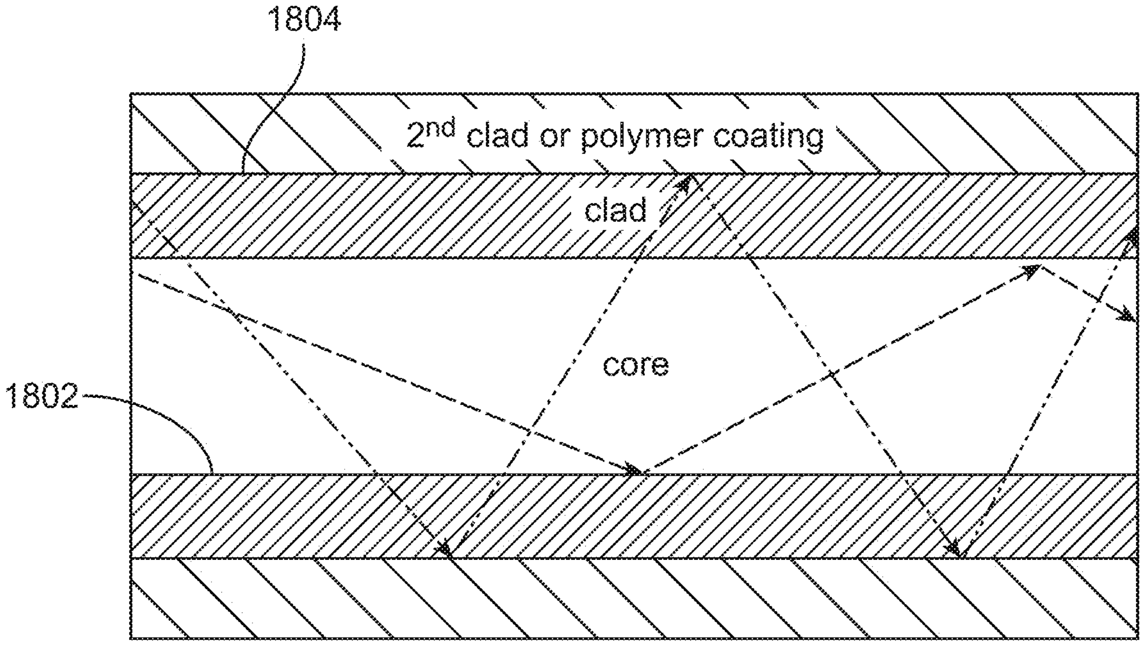

FIGS. 18A and 18B depict aspects of evanescent coupling heating, according to embodiments of the present invention. As shown here, the fiber system 1800 has a cone of acceptance 1892 for a clad and a cone of acceptance 1894 for a core. In some cases, if light power is launched into the core cone acceptance angle (e.g. cone angle $\alpha$), then that light can continue to propagate until it reaches the end of the fiber, experiencing TIR between the core and clad interface 1802 (i.e. not the outer clad interface). In such an operation of a fiber optic delivery system, this may assume that the clad is thick enough to fully contain the evanescent fields. In some cases, power that is launched into the cone angle of acceptance for the clad (e.g. clad angle $\beta$) will produce the desired evanescent fields at the outer first clad-second clad interface 1804. In such an operation of a fiber optic delivery system, this may assume that the second clad is thick enough to fully contain the core-clad evanescent field, otherwise the evanescent field can couple outside the 2nd clad before desired. Adjusting the second clad thickness when it is desired to have power transferred to the tissue can be used to meter how much evanescent power is allowed to couple out of the fiber at a given rate, spreading out the heat more along the fiber length if desired. This embodiment may be particularly applicable to glass clad fibers where it may be difficult to have a sudden interface where the glass clad (1st clad) thickness abruptly changes or is eliminated, due to the fiber optic manufacturing process. Often, the second clad is a polymer clad of some type which is easier to remove or manipulate. The 2nd clad can also have its own cone angle of acceptance. Alternatively, the first clad can be made thin enough so that the evanescent fields from the core-first clad interface bridge across the first clad but are contained by the second clad. In areas where the second clad is eliminated or substantially thin the evanescent fields can leak out of the fiber into the tissue, causing heating. The thickness of the first clad in this situation can control the rate of heat transfer along the length of the fiber. According to some embodiments, a single clad may be used if the clad can be thick enough to contain the evanescent fields where heating is not desired and the clad eliminated or made thin in areas where heating of the tissue is desired. In some instances, the clad or first clad can be referred to as the inner clad, and the second clad can be referred to as the outer clad. In some instances, a fiber optic can include a core, a clad (e.g. $1^{st}$ clad) disposed peripherally to the core, and an absorbing material (e.g. 2nd clad or polymer coating) disposed peripherally to the clad, and an evanescent electromagnetic field extending past a total internal reflection boundary of the clad generates heat in the absorbing material. An exemplary absorbing material can include a medically approved epoxy dyed for enhanced absorption by a medically approved pigment. Graphite can also be used in an absorbing material.

Figure 19A:
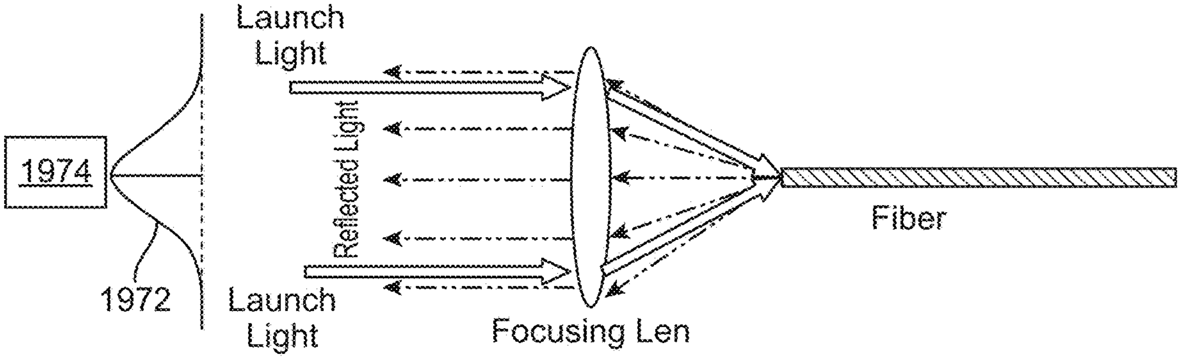
FIGS. 19A and 19B depict aspects of photonic treatment and/or diagnostic methods, according to embodiments of the present invention.
Figure 19B:
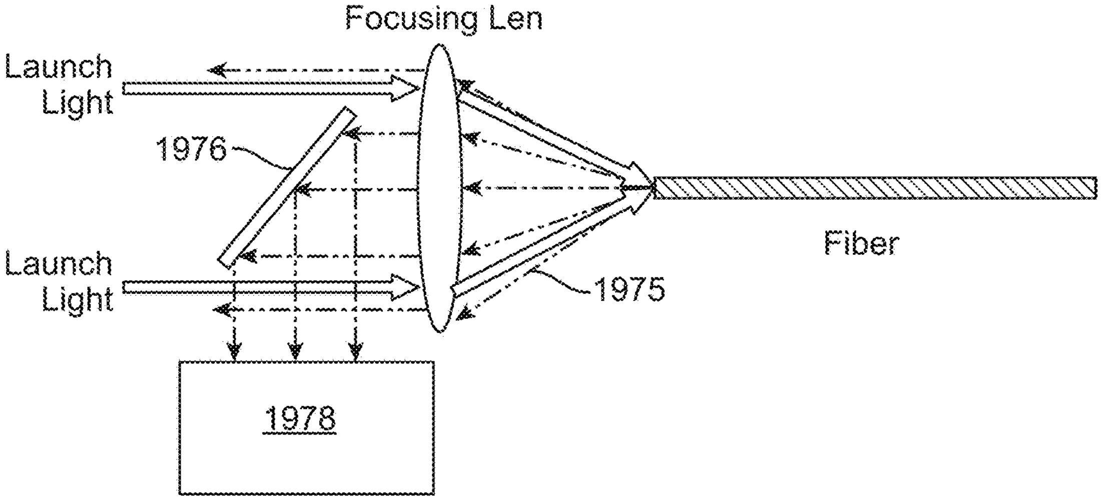

FIG. 19A depicts aspects of an evanescent coupling spectral feedback technique, according to embodiments of the present invention. The fiber may include a core and a clad. In some embodiments, the power is not delivered via the core, but by the clad. The power is launched in the acceptance cone of the clad, but not the acceptance cone of the core. The core is not used to transmit the power beam and can be used to return scattered light back up the fiber for analysis inside the acceptance cone of the core, much like the inverse of the Cladding Light Method described elsewhere herein (e.g. with reference to FIGS. 14A and 14B). The core can also be used to deliver multi-spectral light as described elsewhere herein. This can allow for a stronger diagnostic light signal returned on the fiber since often the core has a much larger cross-sectional area than the clad and the core acceptance cone NA is often larger than the difference between the clad acceptance cone NA and the core acceptance cone NA. The returned beam intensity profile also often is a symmetric monotonically decreasing profile of gaussian or super-gaussian shape with a peak at the center. Thus, it can be advantageous to be able to measure the returned beam at the center versus at the edges as was described elsewhere herein. The backscattered light will be wide angle, but the intensity will be largest at the center and spatial separation of the beam will be easier at the optical elements since the power (launch) beam is substantially excluded from the center of these elements. As shown in FIG. 19A, the reflected light can be at a larger radius on the lens (e.g. focusing lens) used to focus the light into the fiber at the light source. The reflected light can have a reflected light intensity profile 1972, which can be analyzed using a detector or spectral analyzer 1974. In some embodiments, the launch light profile can be like a doughnut or annulus with the center empty, and the reflected light, which fills up the entire circle, can be detected in the doughnut hole where the reflected light will be more intense and provide a stronger signal. As depicted in this embodiment and illustrated by the reflected light intensity profile 1972, the reflected light can be analyzed at the center. As illustrated by the evanescent coupling spectral feedback technique shown in FIG. 19B, a mirror or other optical turning element 1976 can be used to direct the reflected light 1975 toward a detector or spectral analyzer 1978.

In photonic treatments, body tissue can be exposed to very high temperatures in order to treat cancer and other medical conditions. In some cases, localized hyperthermia is used to heat a very small area, which may be in or at a cancer tumor. Exemplary treatments can involve heating the tumor using photonic energy, so as to destroy it, without negatively impacting the surrounding tissue or with minimal negative impact to the surrounding tissue.

In some cases, a photonic generation device (e.g. which includes a laser or other light source) and/or diagnostic device can be further include or be in operative association with a control unit. In some embodiments the control unit may include or be in operative association with a user interface. The control unit can include or be in operative association with one or more processors (e.g. such as processor(s) 1004 depicted in FIG. 20) configured with instructions for performing one or more method steps and operations as described elsewhere herein. Similarly, the control unit may include or be in connectivity with any other component of a computer system (e.g. such as computer system 1000 depicted in FIG. 20).

Figure 20:
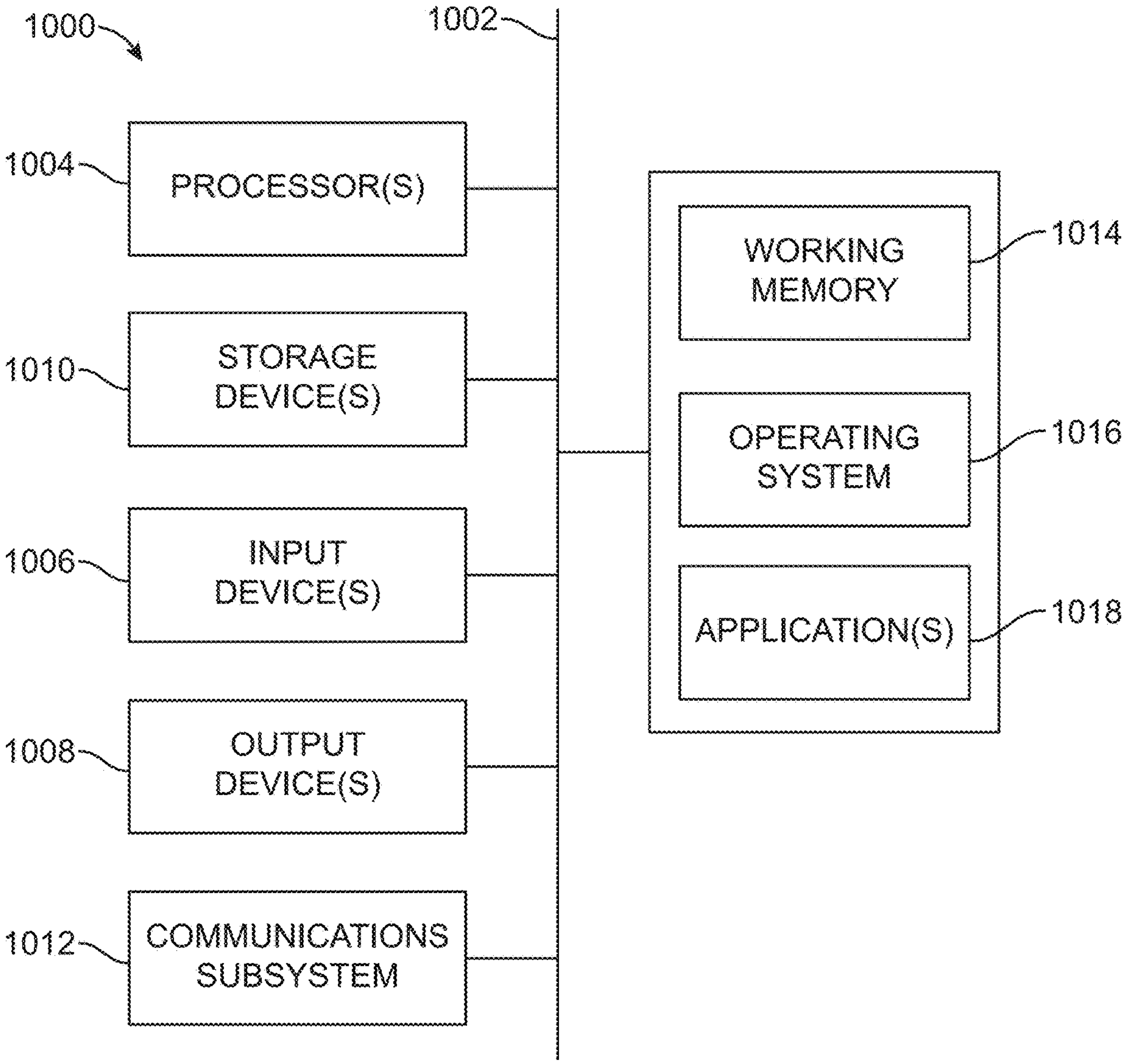
FIG. 20 depicts aspects of photonic treatment and/or diagnostic systems, according to embodiments of the present invention.

FIG. 20 depicts aspects of an exemplary computer system or device 1000 configured for use with any of the treatment and/or diagnostic devices or methods disclosed herein, according to embodiments of the present invention. An example of a computer system or device 1000 may include an enterprise server, blade server, desktop computer, laptop computer, tablet computer, personal data assistant, smartphone, any combination thereof, and/or any other type of machine configured for performing calculations. Any computing devices encompassed by embodiments of the present invention may be wholly or at least partially configured to exhibit features similar to the computer system 1000.

The computer system 1000 of FIG. 10 is shown comprising hardware elements that may be electrically coupled via a bus 1002 (or may otherwise be in communication, as appropriate). The hardware elements may include a processing unit with one or more processors 1004, including without limitation one or more general-purpose processors and/or one or more special-purpose processors (such as digital signal processing chips, graphics acceleration processors, and/or the like); one or more input devices 1006, which may include without limitation a remote control, a mouse, a keyboard, a keypad, a touchscreen, and/or the like; and one or more output devices 1008, which may include without limitation a presentation device (e.g., controller screen, display screen), a printer, and/or the like.

The computer system 1000 may further include (and/or be in communication with) one or more non-transitory storage devices 1010, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer system 1000 can also include a communications subsystem 1012, which may include without limitation a modem, a network card (wireless and/or wired), an infrared communication device, a wireless communication device and/or a chipset such as a Bluetooth device, 802.11 device, WiFi device, WiMax device, cellular communication facilities such as GSM (Global System for Mobile Communications), W-CDMA (Wideband Code Division Multiple Access), LTE (Long Term Evolution), and the like. The communications subsystem 1012 may permit data to be exchanged with a network (such as the network described below, to name one example), other computer systems, controllers, and/or any other devices described herein. In many embodiments, the computer system 1000 can further comprise a working memory 1014, which may include a random access memory and/or a read-only memory device, as described above.

The computer system 1000 also can comprise software elements, shown as being currently located within the working memory 1014, including an operating system 1016, device drivers, executable libraries, and/or other code, such as one or more application programs 1018, which may comprise computer programs provided by various embodiments, and/or may be designed to implement methods, and/or configure systems, provided by other embodiments, as described herein. By way of example, one or more procedures described with respect to the method(s) discussed herein, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code can be stored on a non-transitory computer-readable storage medium, such as the storage device(s) 1010 described above. In some cases, the storage medium might be incorporated within a computer system, such as computer system 1000. In other embodiments, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer system 1000 and/or might take the form of source and/or installable code, which, upon compilation and/or installation on the computer system 1000 (e.g., using any of a variety of generally available compilers, installation programs, compression/decompression utilities, and the like), then takes the form of executable code.

It is apparent that substantial variations may be made in accordance with specific requirements. For example, customized hardware might also be used, and/or particular elements might be implemented in hardware, software (including portable software, such as applets, and the like), or both. Further, connection to other computing devices such as network input/output devices may be employed.

As mentioned elsewhere herein, in one aspect, some embodiments may employ a computer system (such as the computer system 1000) to perform methods in accordance with various embodiments of the disclosure. According to a set of embodiments, some or all of the procedures of such methods are performed by the computer system 1000 in response to processor 1004 executing one or more sequences of one or more instructions (which might be incorporated into the operating system 1016 and/or other code, such as an application program 1018) contained in the working memory 1014. Such instructions may be read into the working memory 1014 from another computer-readable medium, such as one or more of the storage device(s) 1010. Merely by way of example, execution of the sequences of instructions contained in the working memory 1014 may cause the processor(s) 1004 to perform one or more procedures of the methods described herein.

The terms "machine-readable medium" and "computer-readable medium," as used herein, can refer to any non-transitory medium that participates in providing data that causes a machine to operate in a specific fashion. In an embodiment implemented using the computer system 1000, various computer-readable media might be involved in providing instructions/code to processor(s) 1004 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 1010. Volatile media may include, without limitation, dynamic memory, such as the working memory 1014.

Exemplary forms of physical and/or tangible computer-readable media may include a floppy disk, a flexible disk, hard disk, magnetic tape, or any other magnetic medium, a compact disc, any other optical medium, ROM, RAM, and the like, any other memory chip or cartridge, or any other medium from which a computer may read instructions and/or code. Various forms of computer-readable media may be involved in carrying one or more sequences of one or more instructions to the processor(s) 1004 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 1000.

The communications subsystem 1012 (and/or components thereof) generally can receive signals, and the bus 1002 then can carry the signals (and/or the data, instructions, and the like, carried by the signals) to the working memory 1014, from which the processor(s) 1004 retrieves and executes the instructions. The instructions received by the working memory 1014 may optionally be stored on a non-transitory storage device 1010 either before or after execution by the processor(s) 1004.

It should further be understood that the components of computer system 1000 can be distributed across a network. For example, some processing may be performed in one location using a first processor while other processing may be performed by another processor remote from the first processor. Other components of computer system 1000 may be similarly distributed. As such, computer system 1000 may be interpreted as a distributed computing system that performs processing in multiple locations. In some instances, computer system 1000 may be interpreted as a single computing device, such as a distinct laptop, desktop computer, or the like, depending on the context.

A processor may be a hardware processor such as a central processing unit (CPU), a graphic processing unit (GPU), or a general-purpose processing unit. A processor can be any suitable integrated circuits, such as computing platforms or microprocessors, logic devices and the like. Although the disclosure is described with reference to a processor, other types of integrated circuits and logic devices are also applicable. The processors or machines may not be limited by the data operation capabilities. The processors or machines may perform 512 bit, 256 bit, 128 bit, 64 bit, 32 bit, or 16 bit data operations.

Each of the calculations or operations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described herein. All features of the described systems are applicable to the described methods mutatis mutandis, and vice versa. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

According to some embodiments, machine-readable code instructions for, and/or data generated or used by, treatment devices, diagnostic devices, and/or computing devices (which may include smart phones or other mobile computing devices) can be stored on or executed by any of a variety of computing modalities, including without limitation personal computers, servers (e.g. hosted and/or privately owned servers), internet connections, cloud hosts, cloud based storage, and the like.

As described elsewhere herein, a treatment device and/or diagnostic device can include or be in operative association with a control unit. In some embodiments the control unit may include or be in operative association with a user interface. The control unit can include or be in operative association with one or more processors configured with instructions for performing one or more method steps (e.g. delivering photonic energy to a treatment location of a patient. A control unit may include or be in connectivity with any component of a computer system.

All publications, patents, patent applications, journal articles, books, technical references, and the like mentioned in this specification are herein incorporated by reference to the same extent as if each individual publication, patent, patent application, journal article, book, technical reference, or the like was specifically and individually indicated to be incorporated by reference.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a patient presenting with a cancerous tumor, the method comprising:

placing a fiber optic within the tumor of the patient, wherein the fiber optic is coupled with an absorber mechanism, and wherein the absorber mechanism also is placed within the tumor of the patient; and delivering photonic energy via the fiber optic to the absorber mechanism, wherein the photonic energy exits a distal end of the fiber optic and is absorbed by the absorber mechanism where the photonic energy is converted to heat energy, and wherein the heat energy in the absorber mechanism destroys tissue of the tumor of the patient, wherein the absorber mechanism reaches 225° C. in 60 seconds with one watt of power absorption or wherein tissue within the tumor is heated to 225° C. while tissue adjacent the tumor is not heated above 55.8° C., and wherein the fiber optic is coupled with the absorber mechanism with an optical epoxy, a ceramic epoxy, soldering, brazing, or a cold weld.

2. The method according to claim 1, wherein the absorber mechanism comprises a material selected from the group consisting of graphite, steel, a steel alloy, copper, aluminum, silver, molybdenum, iron, titanium, and gold.

3. The method according to claim 1, wherein the fiber optic comprises a core and a clad.

4. The method according to claim 1, wherein a needle is inserted into the patient, and the step of placing the fiber optic within the tumor of the patient comprises advancing the fiber optic within the inserted needle.

5. A method of treating a patient presenting with a cancerous tumor, the method comprising:

placing a fiber optic within the tumor of the patient, wherein the fiber optic is coupled with an absorber mechanism, and wherein the absorber mechanism also is placed within the tumor of the patient; and delivering photonic energy via the fiber optic to the absorber mechanism, wherein the photonic energy exits a distal end of the fiber optic and is absorbed by the absorber mechanism where the photonic energy is converted to heat energy, and wherein the heat energy in the absorber mechanism destroys tissue of the tumor of the patient, wherein the absorber mechanism reaches 225° C. in 60 seconds with one watt of power absorption or wherein tissue within the tumor is heated to 225° C. while tissue adjacent the tumor is not heated above 55.8° C., wherein the absorber mechanism has a thermal coefficient of expansion, and wherein the fiber optic is physically coupled with the absorber mechanism with a coating material, the coating material having a thermal coefficient of expansion that is larger than the thermal coefficient of expansion of the absorber mechanism.

6. The method according to claim 5, wherein the coating material comprises an acrylate.

7. The method according to claim 1, wherein the absorber mechanism comprises a graphite rod.

8. The method according to claim 1, wherein the absorber mechanism comprises gold and the photonic energy delivered via the fiber optic has a wavelength of 355 nm or 450 nm.

9. The method according to claim 1, wherein the absorber mechanism reaches 225° C. in 60 seconds with one watt of power absorption.

10. The method according to claim 1, wherein tissue within the tumor is heated to 225° C. while tissue adjacent the tumor is not heated above 55.8° C.

11. The method according to claim 1, wherein the absorber mechanism comprises a blind aperture, and wherein a distal end of the fiber optic terminates within the blind aperture.

* * * * *